US010722660B2

(12) United States Patent
Van Oudenallen

(10) Patent No.: US 10,722,660 B2
(45) Date of Patent: Jul. 28, 2020

(54) FLUID WARMING SYSTEM

(71) Applicant: THE SURGICAL COMPANY INTERNATIONAL B.V., Amersfoort (NL)

(72) Inventor: Robertus Gerardus Van Oudenallen, Vleuten (NL)

(73) Assignee: THE SURGICAL COMPANY INTERNATIONAL B.V., Amersfoort (NL)

( * ) Notice: Subject to any disclaimer, the term of this patent is extended or adjusted under 35 U.S.C. 154(b) by 526 days.

(21) Appl. No.: 15/156,794

(22) Filed: May 17, 2016

(65) Prior Publication Data

US 2017/0333630 A1 Nov. 23, 2017

(51) Int. Cl.
| | | |
|---|---|---|
| *A61M 5/44* | (2006.01) | |
| *A61M 5/172* | (2006.01) | |
| *A61M 5/168* | (2006.01) | |

(52) U.S. Cl.
CPC ........ *A61M 5/445* (2013.01); *A61M 5/16886* (2013.01); *A61M 5/172* (2013.01); *A61M 2205/18* (2013.01); *A61M 2205/3368* (2013.01); *A61M 2205/36* (2013.01); *A61M 2205/3653* (2013.01); *A61M 2205/502* (2013.01); *A61M 2205/52* (2013.01)

(58) Field of Classification Search
CPC .. A61M 5/172; A61M 5/16886; A61M 5/445; A61M 2205/502; A61M 2205/18; A61M 2205/3368; A61M 2205/52; A61M 5/44; A61M 2205/36; A61M 2205/3653
See application file for complete search history.

(56) References Cited

U.S. PATENT DOCUMENTS

| | | | | |
|---|---|---|---|---|
| 1,794,215 A | * | 2/1931 | Titus | ................. A61M 5/16877 604/506 |
| 4,772,778 A | | 9/1988 | Ogawa | |
| 6,175,688 B1 | * | 1/2001 | Cassidy | ................ A61M 5/365 392/470 |

(Continued)

*Primary Examiner* — Jenna Zhang
(74) *Attorney, Agent, or Firm* — Nixon & Vanderhye P.C.

(57) ABSTRACT

There is disclosed a fluid warming system (300) for warming intravenous fluid, comprising: a heater unit (304), including a heating element (314) and at least one temperature sensor; a heat exchanger unit (302), removably attachable to the heater unit (304), which includes an inlet (306) and an outlet (308) through which the fluid can pass, and a controller (316), programmed: to receive at least one temperature measurement ($T_{CI}$, $T_{CO}$) from said at least one temperature sensor in the heater unit (304); to compute a fluid flow rate (q), corresponding to the rate of flow of fluid from the inlet (306) to the outlet (308) of the heat exchanger unit (302), in dependence on the amount of electrical power ($P_H$) supplied to the heating element and said at least one temperature measurement ($T_{CI}$, $T_{CO}$); and to control the electrical power ($P_H$) supplied to the heating element in dependence on the computed fluid flow rate (q).

23 Claims, 19 Drawing Sheets

(56) References Cited

U.S. PATENT DOCUMENTS

| | | | | |
|---|---|---|---|---|
| 8,444,592 B2* | 5/2013 | Williams | ............... | A61M 5/172 |
| | | | | 604/27 |
| 2001/0011585 A1* | 8/2001 | Cassidy | ................ | A61M 5/365 |
| | | | | 165/46 |
| 2002/0021741 A1* | 2/2002 | Faries, Jr. | ............... | G01K 11/12 |
| | | | | 374/141 |
| 2005/0070845 A1* | 3/2005 | Faries, Jr. | ............. | A61M 5/148 |
| | | | | 604/98.01 |
| 2006/0222350 A1* | 10/2006 | Cassidy | .................. | A61M 5/44 |
| | | | | 392/470 |
| 2008/0021377 A1* | 1/2008 | Kienman | ................ | A61M 5/44 |
| | | | | 604/29 |
| 2016/0271342 A1* | 9/2016 | Bronkhorst | ............. | A61M 5/44 |

\* cited by examiner

TOP VIEW

CROSS SECTION AT X-X'

BOTTOM VIEW

TOP VIEW

SIDE VIEW

END VIEW

TOP VIEW

BOTTOM VIEW

FLUID WARMING SYSTEM

BACKGROUND OF THE INVENTION

Field of the Invention

The present invention relates to a fluid warming system, and method of operating same. The invention is particularly applicable to the warming of intravenous (IV) fluids for delivery to a patient. The invention may also be applied to refrigeration systems.

Description of the Related Art

In some cases it is convenient or necessary to use a fluid warmer to heat a fluid to a target temperature or range of temperatures, for example to warm intravenous (IV) fluids to body temperature before delivery to a patient, or to avoid ice forming within water pipes that may be exposed to sub-zero temperatures, or to prevent condensation of steam or other gases in certain parts of a chemical plant, and so on. The design of a fluid warmer may be complicated by an unknown or varying flow rate of fluid, a range of target temperatures, and may also be complicated by an unknown or varying temperature of the fluid entering the fluid warmer, for example.

One design for an IV fluid warmer is given for example in U.S. Pat. No. 4,772,778, which discloses a system in which an IV line (that is, a thin tube carrying IV fluid) is placed within a serpentine groove in a heater casing, and the electric input to the heater is controlled on the basis of the temperature determined by a "fluid-temperature thermistor", so as to raise the temperature of the fluid to a predetermined temperature. In this system, the serpentine shape of the groove in the heater allows a relatively long length of IV line to be exposed to the heater, increasing the amount of heat transferred to the fluid in the IV line. This type of device can suffer from several disadvantages, however, including the fact that a longer fluid path introduces more lag in the control of the heater, and the fact that a change in flow rate is more prone to cause either overheating of one part of the fluid, or underheating of another. In addition, the relatively poor thermal conductivity of the IV line reduces the efficiency of the system and can introduce further lag in the control of the heater. Furthermore, threading the IV line into the groove in the heater can be a time-consuming and difficult task in a clinical setting.

Some fluid warming systems have improved usability by providing a dedicated fluid channel for heating the fluid, for example within a disposable cassette that can be attached to a heater unit. Such a cassette may have an inlet and outlet to which IV lines can be attached. Conventionally the heater element of a fluid warmer is controlled in dependence on a measured fluid outlet temperature, and temperature sensors are located as near as possible to the fluid outlet, including within the fluid itself. This latter arrangement can cause problems with contamination of the fluid, and there can otherwise be issues with cost and complexity, for example if an interface is required to transmit temperature measurements from the cassette to the control system. However, accurate temperature measurements or derivations are important if controlling a heater directly in dependence on such temperatures, and one would normally expect the performance of the heater control system to be worsened if temperature sensors were moved further away from the fluid.

The present invention seeks to address these and other problems in the prior art.

SUMMARY OF THE INVENTION

In a first aspect of the invention, there is provided a fluid warming system for warming intravenous fluid, comprising: a heater unit, including a heating element and at least one temperature sensor; a heat exchanger unit, removably attachable to the heater unit, which includes an inlet and an outlet through which the fluid can pass, and a controller, programmed: to receive at least one temperature measurement from said at least one temperature sensor in the heater unit; to compute a fluid flow rate, corresponding to the rate of flow of fluid from the inlet to the outlet of the heat exchanger unit, in dependence on the amount of electrical power supplied to the heating element and said at least one temperature measurement; and to control the electrical power supplied to the heating element in dependence on the computed fluid flow rate.

In a second aspect of the invention, the controller is programmed: to compute an inlet heat flux corresponding to the heat flux between the heating element and the fluid in the vicinity of the inlet of the heat exchanger unit; to compute an outlet heat flux corresponding to the heat flux between the heating element and the fluid in the vicinity of the outlet of the heat exchanger unit; to compute an inlet fluid temperature in dependence on the computed inlet heat flux; to compute an outlet fluid temperature in dependence on the computed outlet heat flux: and to compute the fluid flow rate in dependence on the computed inlet and outlet fluid temperature.

In a third aspect of the invention there is provided a (computer-implemented) method of operating a fluid warming system to warm intravenous fluid, the fluid warming system comprising a heater unit, including a heating element and at least one temperature sensor, and a heat exchanger unit, removably attachable to the heater unit and including an inlet and an outlet through which the fluid can pass, and the method comprising: receiving at least one temperature measurement from said at least one temperature sensor in the heater unit; computing a fluid flow rate, corresponding to the rate of flow of fluid from the inlet to the outlet of the heat exchanger unit, in dependence on the amount of electrical power supplied to the heating element and said at least one temperature measurement; and controlling the electrical power supplied to the heating element in dependence on the computed fluid flow rate.

Although the embodiments of the invention described herein with reference to the drawings may comprise computer-related methods or apparatus, the invention may also extend to program instructions, particularly program instructions on or in a carrier, adapted for carrying out the processes of the invention or for causing a computer to perform as the computer apparatus of the invention. Programs may be in the form of source code, object code, a code intermediate source, such as in partially compiled form, or any other form suitable for use in the implementation of the processes according to the invention. The carrier may be any entity or device capable of carrying the program instructions.

For example, the carrier may comprise a storage medium, such as a ROM, for example a CD ROM or a semiconductor ROM, or a magnetic recording medium, for example a floppy disc, hard disc, or flash memory, optical memory, and so on. Further, the carrier may be a transmissible carrier such as an electrical or optical signal which may be conveyed via electrical or optical cable or by radio or other means. When a program is embodied in a signal which may be conveyed directly by cable, the carrier may be constituted by such cable or other device or means.

Although various aspects and embodiments of the present invention are described separately herein, any of the aspects and features of the present invention can be used in conjunction with any other aspect, embodiment or feature where appropriate. For example apparatus features may where appropriate be interchanged with method features. References to single entities should, where appropriate, be considered generally applicable to multiple entities and vice versa. Unless otherwise stated herein, no feature described herein should be considered to be incompatible with any other, unless such a combination is clearly and inherently incompatible. Accordingly, it should generally be envisaged that each and every separate feature disclosed in the introduction, description and drawings is combinable in any appropriate way with any other unless (as noted above) explicitly or clearly incompatible.

BRIEF DESCRIPTION OF THE DRAWINGS

An example embodiment of the present invention will now be illustrated with reference to the following figures in which.

DETAILED DESCRIPTION OF THE INVENTION

Figure 1:
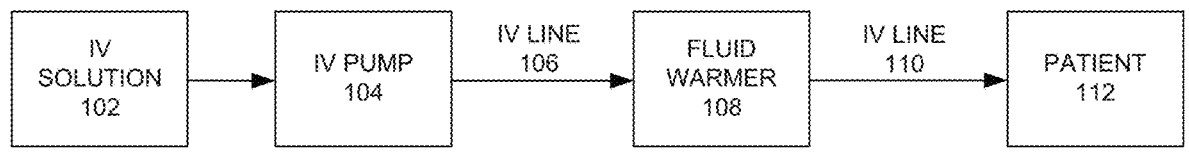
FIG. 1 is an overview of a typical application of a fluid warming system.

Various embodiments will be described first in overview, and later on in greater detail. Reference numerals included below relate to an exemplary embodiment illustrated in FIG. 3 and described in more detail below, and are not intended to be limiting in any way.

In a first embodiment, there is provided a fluid warming system 300 for warming intravenous fluid, comprising: a heater unit 304, including a heating element 314 and at least one temperature sensor; a heat exchanger unit 302, removably attachable to the heater unit 304, which includes an inlet 306 and an outlet 308 through which the fluid can pass, and a controller 316, programmed: to receive at least one temperature measurement ($T_{CI}$, $T_{CO}$) from said at least one temperature sensor in the heater unit 304; to compute a fluid flow rate (q), corresponding to the rate of flow of fluid from the inlet 306 to the outlet 308 of the heat exchanger unit 302, in dependence on the amount of electrical power ($P_H$) supplied to the heating element 314 and said at least one temperature measurement ($T_{CI}$, $T_{CO}$); and to control the electrical power ($P_H$) supplied to the heating element 314 in dependence on the computed fluid flow rate (q).

This can be advantageous because the actual fluid temperatures are derived, and thus no direct (in-fluid) measurement of fluid temperature is required, preventing contamination of the fluid (a particular concern for IV fluids). In addition, controlling the heating element in dependence on fluid flow rates can improve the performance of the controller, since using fluid flow rates provides an element of feed-forward control and can reduce the sensitivity of the control system to changes in fluid temperature caused (for example) by changes in flow rate.

The computation of the fluid flow rate may use a derived or measured value of the electrical power supplied to the heater element, for example based on a measurement of voltage, current and/or resistance, or based on a model of expected power based on an input voltage or current, and so on. The power may be an instantaneous or historic value or, for example, an averaged or modelled value which may seek to eliminate or reduce transient effects or spikes in voltage or current which may lead to a false evaluation of fluid flow rate. Appropriate smoothing may be applied to an estimate or measurement (derived or otherwise) of applied electrical power based on the maximum variability or differential of the fluid flow rate.

The controller is preferably provided outside the heater unit and more preferably remote from the heater unit and/or patient who is receiving the intravenous fluids, in which case a control (and optionally power) connection is provided between the controller and the heater unit. In another embodiment the controller can be provided within the heater unit (or even heat exchanger unit). Though described and defined herein with reference to warming intravenous fluids, the products, methods and systems described herein may extend to alternative embodiments in respect of warming other types of fluid (which may not be limited to liquids). The heater unit may comprise a safety controller, separate to the aforesaid (main) controller, receiving readings from at least one of the temperature sensors at outlet (preferably a dedicated sensor not connected to and/or used by the main controller). The controller is preferably located physically remote from the safety controller, for example as part of a docking station for the heater unit and/or mountable/attachable unit entirely separate from the heater unit. The safety controller preferably operates autonomously from the main controller, though it may have means for communicating briefly during start-up, and the like.

The term 'programmed' should be construed as covering embodiments which are partially or fully implemented in hardware rather than software, as is explained in more detail later. It will be appreciated that the embodiments described herein may also apply to a refrigeration system, with references to heating being replaced by references to cooling, and so on.

Preferably the controller is further programmed: to compute an inlet fluid temperature ($T_I$) in dependence on a first said at least one temperature measurement ($T_{CI}$), measured in thermal proximity to the inlet 306, and the electrical power ($P_H$) supplied to the heater element 314; to compute an outlet fluid temperature ($T_O$) in dependence on a second said at least one temperature measurement ($T_{CO}$), measured in thermal proximity to the outlet 308, and the electrical power ($P_H$) supplied to the heater element 314; and to compute the fluid flow rate (q) in dependence on the computed inlet and outlet fluid temperature ($T_I$, $T_O$). In this scheme, there is no need to compute heat fluxes, simplifying the computation process.

Preferably the controller is further programmed to compute said inlet fluid temperature ($T_I$) as the difference between a value dependent on the first said at least one temperature measurement ($T_{CI}$) and a value proportional to the electrical power supplied to the heater element ($P_H$); and to compute said outlet fluid temperature ($T_O$) as the difference between a value dependent on the second said at least one temperature measurement ($T_{CO}$) and a value proportional to the electrical power ($P_H$) supplied to the heater element.

For example, the computation may be of the form: $T_I = f(T_{CI}) - C_{IN} \times P_H$ (where $T_I$ is the inlet fluid temperature, $T_{CI}$ is the contact inlet temperature measurement, $f(T_{CI})$ is some function of $T_{CI}$, $P_H$ is the heater power, and $C_{IN}$ is an appropriate constant giving reasonable accuracy over the relevant range of operating conditions), and similarly for $T_O$ with references to inlet replaced by references to outlet as appropriate.

More preferably the controller is further programmed to compute said value dependent on the first said at least one temperature measurement as a value proportional to the first said at least one temperature measurement added to an inlet temperature correction value; and to compute said value dependent on the second said at least one temperature measurement as a value proportional to the second said at least one temperature measurement added to an outlet temperature correction value. The inlet and/or outlet temperature correction values may be fixed constants or may vary in dependence on operating conditions (such as external measured temperature, characteristics of the fluid, type of tube, and so on), and are preferably determined for particular combinations of heater unit and heat transfer unit by experimental analysis of the operation of the units. Different constants may be stored and/or used in the event that different types of heat transfer unit are useable in the system, for example.

In one specific embodiment the computation may be of the form: $T_I = (C_{IN1} \times T_{CI} + C_{IN2}) - C_{IN3} \times P_H$ (where $T_I$ is the inlet fluid temperature, $T_{CI}$ is the contact inlet temperature measurement, $P_H$ is the heater power, and $C_{IN1}$, $C_{IN2}$ and $C_{IN3}$ are appropriate constants giving reasonable accuracy over the relevant range of operating conditions), and similarly for $T_O$. with references to inlet replaced by references to outlet as appropriate. The inlet/outlet temperature correction value (corresponding to $C_{IN3}$ here) is typically negative.

In another specific embodiment, the inlet and outlet fluid temperatures are computed simply by subtracting the electrical power, multiplied by an appropriate constant for the particular configuration at the inlet/outlet, from a calibrated version of the contact/surface temperature reading at the inlet/outlet respectively. That is, the computation may be of the form $T_I = C_{IN1} \times T_{CI} \, C_{IN2} \times P_H$ (where $T_I$ is the inlet fluid temperature, $T_{CI}$ is the contact inlet temperature measurement, $P_H$ is the heater power, and $C_{IN1}$ and $C_{IN2}$ are appropriate constants giving reasonable accuracy over the relevant range of operating conditions). In this or other embodiments, the result may also be offset by a constant value, and either or both of the inlet/outlet fluid temperatures and the heater power may be raised to an appropriate constant (or otherwise) exponent, or subject to any other appropriate linear or non-linear function so as to obtain more sophisticated control.

The temperature at the heat exchanger unit is typically derived from a temperature measured in thermal proximity to the heat exchanger unit rather than physically adjacent to or within the heat exchanger unit. Accordingly, said at least one temperature sensor in the heater unit may comprise: at least one inlet temperature sensor 1008 in thermal proximity to the inlet 306 of the heat exchanger unit 302, when attached; at least one outlet temperature sensor 1010, 1012 in thermal proximity to the outlet 308 of the heat exchanger unit 302, when attached. The heater unit preferably further comprises at least one heater temperature sensor in thermal proximity to the heating element, which can provide additional protection against overheating and the like. The controller may be programmed to compute the inlet heat flux and outlet heat flux in dependence on measurements received from said at least one heater temperature sensor, said at least one inlet temperature sensor, and said at least one outlet temperature sensor.

By providing the temperature sensors within the heater unit, sensors need not be provided within the heat exchanger unit, obviating the need for a data interface or the like, and allowing the cost of the transport unit (which may for example be disposable or otherwise mass-produced) to be kept to a minimum. The inlet and outlet temperature sensors are preferably located in thermal proximity (if not also positional proximity) to a heat transfer surface that, in use, contacts the heat exchanger unit (and is preferably in close thermal proximity also to the fluid within the heat exchanger unit, in use).

Alternatively or additionally, temperatures may be derived or measured within the heat exchanger unit and optionally within the fluid (though this has certain disadvantages as explained above). In this case, the derivation of heat fluxes and fluid temperatures may, for example, be used as a redundancy or verification check on a directly measured (or otherwise derived) reading.

The controller may be programmed to compute the average temperature readings from a plurality of related temperature sensors, and to use said average in subsequent computations. The controller may be programmed to compare at least one temperature measurement with a threshold temperature and to output an overheat signal if said at least one temperature measurement exceeds said threshold temperature. The controller may be programmed to output an error signal if a plurality of related temperature measurements differ by more than a threshold amount.

The heat exchanger unit may be a simple fluid conduit, such as a tube or similar, or it may be a cassette, disposable or otherwise, or any other structure having an internally defined fluid path in thermal contact with the heater unit. Preferably the surface area per length of conduit is larger within the heat exchanger unit than outside, and more preferably the surface area per unit length on the side of the conduit facing the heater unit is larger within the heat exchanger unit than outside. Preferably the fluid conduit within the heat exchanger unit is substantially planar, or otherwise shaped to maximise the heat transfer with the heater unit.

The heater unit may comprise at least two outlet temperature sensors, and the controller may be programmed to compute a respective at least two outlet fluid temperatures and a respective at least two fluid flow rates.

By this means, the controller can average the outputs of the temperature sensors, choose most plausible measurement, or shut down the heater and/or raise an alarm if any of the measured or derived temperatures or derived fluid flow rates diverge by an appropriate amount, even if individually the measured and derived values are within acceptable bounds. A similar feature may be provided with respect to inlet temperature sensors, or any other temperature sensors.

By deriving independent values for the outlet fluid temperature and fluid flow rate, redundancy can be provided. This is especially useful for the outlet temperature measurements because the outlet fluid temperature is the most critical with respect to avoiding overheating of the fluid.

As mentioned above, preferably none of the temperature sensors are in physical contact with the fluid. In particular, preferably there are no temperature sensors within or, more preferably, physically contacting the heat exchanger unit or a fluid conduit therein.

The heater unit may further comprise a first heat transfer surface for engagement with a corresponding second heat transfer surface of the heat exchanger unit, for effecting heat transfer between the heating element and the fluid when the heat exchanger unit is attached to the heater unit.

The heat transfer surface(s) are preferably flat and thermally conductive so as to maximise heat transfer and minimise path length. The inlet and outlet temperature sensors are preferably in thermal proximity to the heat transfer surface. The surface could also be serpentine or have another configuration if, for example a longer heat transfer surface was desired, though generally this may not be as it may involve more lag and attendant control issues (but may be appropriate for higher and/or more predictable flow rates).

The controller may be programmed, in at least one operating mode, to control the electrical power ($P_H$) supplied to the heating element 314 so as to cause it to converge on a target heater power ($P_T$) selected in dependence on the computed fluid flow rate (q). The control system may for example incorporate any appropriate variation of proportional, integral and/or derivative (PID) elements. The controller may for example make corrections to target power as necessary depending on feedback from derived or measured temperature values and flow rates and the like.

The target heater power ($P_T$) may be selected in accordance with an expected relation between the heater power and a target outlet fluid temperature at the computed fluid flow rate. The relation may for example be a formula that relates a target heater power $P_T$ to a selected target outlet fluid temperature $T_O$ and a computed fluid flow rate q, and may be of the form $P_T=f(T_O, q)$. The formula may for example depend on a measured or derived inlet temperature, either at the heat exchanger unit or further back in the fluid flow path, or on an ambient temperature which may be a reasonable approximation of the fluid inlet temperature if the fluid has effected a significant amount of heat transfer with the environment. A formula may alternatively be specified in terms of a desired temperature increase within the transport unit, and so on.

In an alternative embodiment, the controller 316 may be programmed, in at least one operating mode, to control the electrical power ($P_H$) supplied to the heating element 314 so as to cause the computed outlet fluid temperature to converge on a target temperature. The target temperature may for example be selected in dependence on the computed fluid flow rate, and may thus for example be varied dynamically and/or adapt to the prevailing conditions in the fluid or otherwise.

The controller 316 may be programmed, in at least one further operating mode, to cease (or reduce) the supply of electrical power ($P_H$) to the heating unit, for example in response to a potential or actual overheat condition (relating to a measured or derived temperature or power in or proximate the fluid, or otherwise). Preferably the controller will revert to said at least one operating mode when operating conditions are suitable, for example if an overheat condition is cleared or reduced. In the further operating mode, the computation/derivation of various properties such as heat fluxes, inlet and outlet temperatures and fluid flow rates may be suspended, or may be continued using alternative measurements or information. The further operating mode may, for example, be triggered by thermal or other cut-outs, and the like, for example in the event of a measured or derived temperature exceeding a threshold. In the further operating mode it may not be possible to continue a computation or derivation of fluid flow rate, and the control scheme may be simpler but less accurate. The controller may for example use assumptions on the current state of the system (or determine likely bounds on the state) based on the state of the previous operating mode.

The heater unit 304 is preferably electrically isolated from the heat exchanger unit 302. In particular, there may not be provided electrical contacts, for example for transmitting temperature readings to the heater unit. This can be beneficial in certain environments, and particularly medical environments, and can improve operator and electrical safety and the like. The heater unit may also be electromagnetically isolated, at least insofar as there are no radio-frequency or other transmissions between the heater unit and heat exchanger unit (or other devices), which can be beneficial in certain settings such as hospitals and the like (due to the risk of interfering with sensitive electrical devices).

Preferably the heating element 314 includes a plurality of sub-elements 1004, 1006, and a different amount of electrical power is supplied to different sub-elements 1004, 1006 (according to a fixed ratio or dynamically and/or independently variable, for example), preferably wherein a greater amount of electrical power is supplied to a sub-element in the vicinity of the inlet 306 of the heat exchanger unit 302 than is supplied to a sub-element in the vicinity of the outlet of the heat exchanger unit. This can limit the boundary layer temperatures of the fluid in contact with the conduit walls because in some parts (typically at the inlet) the fluid is colder and can absorb more heat. The sub-elements may be discrete and electrically isolated from each other, or may be provided by varying resistance or other properties of the heating element, for example in a continuous variation of electrical properties from inlet to outlet (or otherwise), such that the sub-elements are nominal rather than discretely defined. In some embodiments the controller may in addition control the division of electrical power between sub-elements, for example as a consequence of a change of flow rate or after changing the target heater power, so as to provide more sophisticated control over fluid temperatures within the heat exchanger following the transition, and so on. For example, if the inlet fluid temperature drops suddenly, inlet-side heater conditions can be varied to accommodate the change while leaving the outlet-side heater conditions unchanged so as to avoid overheating the already-warmed fluid in later stages of the heat exchanger unit.

The heater unit, heat exchanger unit and controller can all be provided in independent form as appropriate. For example, there may be provided a heat exchanger unit, for use with and removably attachable to a heater unit as aforesaid, the heat exchanger unit comprising an inlet and an outlet, and a heat transfer surface for transferring heat between the heater unit and fluid passing between the inlet and the outlet of the heat exchanger unit.

The heat exchanger unit 302 is preferably connectable to a fluid conduit for transferring the fluid to or from a fluid channel within the heat exchanger unit 302, wherein the surface area per length of the fluid channel is larger than the surface area per length of fluid conduit.

In an alternative embodiment which can provide more sophisticated control at the expense of increased computational complexity, the controller is programmed: to compute an inlet heat flux ($Q_I$) corresponding to the heat flux between the heating element 314 and the fluid in the vicinity of the inlet 306 of the heat exchanger unit 302; to compute an outlet heat flux ($Q_O$) corresponding to the heat flux between the heating element 314 and the fluid in the vicinity of the outlet 308 of the heat exchanger unit 302; to compute an inlet fluid temperature ($T_I$) in dependence on the computed inlet heat flux ($Q_I$); to compute an outlet fluid temperature ($T_O$) in dependence on the computed outlet heat flux ($Q_O$); and to compute the fluid flow rate (q) in dependence on the computed inlet and outlet fluid temperature ($T_I$, $T_O$).

Preferably, at least one of the inlet and outlet heat fluxes ($Q_I$, $Q_O$) is computed as a ratio of the electrical power ($P_{HI}$, $P_{HO}$) supplied to the heater element in the vicinity of the inlet or outlet respectively, and the area of the heater element ($A_{HI}$, $A_{HO}$) exposed to the heat exchanger unit in the vicinity of the inlet or outlet respectively. More preferably, inlet and outlet heat fluxes and/or inlet and outlet fluid temperatures are computed without reference to any temperature measurement. A correction factor (multiplying, adding or subtracting term, and the like) may be applied to the ratio.

Alternatively, at least one of the inlet and outlet heat fluxes ($Q_I$, $Q_O$) may be computed in dependence on a temperature difference between the heating element 314 and the heat exchanger unit 302 in the vicinity of the inlet 306 and outlet 308 respectively (and preferably as the ratio of relevant heat transfer coefficient to the temperature difference). The temperature difference may be measured or derived. In this variant the controller may be programmed to compute a heat transfer coefficient between the heater unit and the heat exchanger unit. The heat fluxes are preferably computed in dependence on the computed heat transfer coefficient. The computed heat transfer coefficient is preferably computed in dependence on at least one of an average temperature at the heating element and an average temperature at or in thermal proximity to the heat exchanger unit.

In another embodiment there is provided a (computer-implemented) method of operating a fluid warming system 300 to warm intravenous fluid, the fluid warming system comprising a heater unit 304, including a heating element 314 and at least one temperature sensor, and a heat exchanger unit 302, removably attachable to the heater unit 304 and including an inlet 306 and an outlet 308 through which the fluid can pass, and the method comprising: receiving at least one temperature measurement from said at least one temperature sensor in the heater unit 304; computing a fluid flow rate (q), corresponding to the rate of flow of fluid from the inlet 306 to the outlet 308 of the heat exchanger unit, in dependence on the amount of electrical power ($P_H$) supplied to the heating element 314 and said at least one temperature measurement; and controlling the electrical power ($P_H$) supplied to the heating element 314 in dependence on the computed fluid flow rate (q).

Although the embodiments described above with reference to the drawings may comprise computer-related methods or apparatus, embodiments may also extend to program instructions, particularly program instructions on or in a carrier, adapted for carrying out the processes of the invention or for causing a computer to perform as the computer apparatus of the invention. Programs may be in the form of source code, object code, a code intermediate source, such as in partially compiled form, or any other form suitable for use in the implementation of the processes according to the invention. The carrier may be any entity or device capable of carrying the program instructions.

For example, the carrier may comprise a storage medium, such as a ROM, for example a CD ROM or a semiconductor ROM, or a magnetic recording medium, for example a floppy disc, hard disc, or flash memory, optical memory, and so on. Further, the carrier may be a transmissible carrier such as an electrical or optical signal which may be conveyed via electrical or optical cable or by radio or other means. When a program is embodied in a signal which may be conveyed directly by cable, the carrier may be constituted by such cable or other device or means.

The various embodiments will now be described in more detail.

FIG. 1 is an overview of a typical application of a fluid warming system, in which an intravenous (IV) solution 102, which may for example be an aqueous solution of one or more medicines, is pumped by an IV pump 104 along an IV line 106 through a fluid warmer 108 and then along a further IV line 110 for intravenous insertion into the bloodstream of a patient 112. Other configurations and applications are of course possible, but a common requirement is to have the fluid at or near a target temperature at the outlet of the fluid warmer. In the case of IV fluids, an outlet temperature typically in the region of 37-41° C. is desired. The IV solution may typically be presented at room temperature at around 20° C., but this temperature may vary. The flow rate of the IV fluid is typically controlled depending on the particular medicine or other fluid to be dispensed, and in dependence on properties of a patient or other end use of the fluid.

Figure 2:
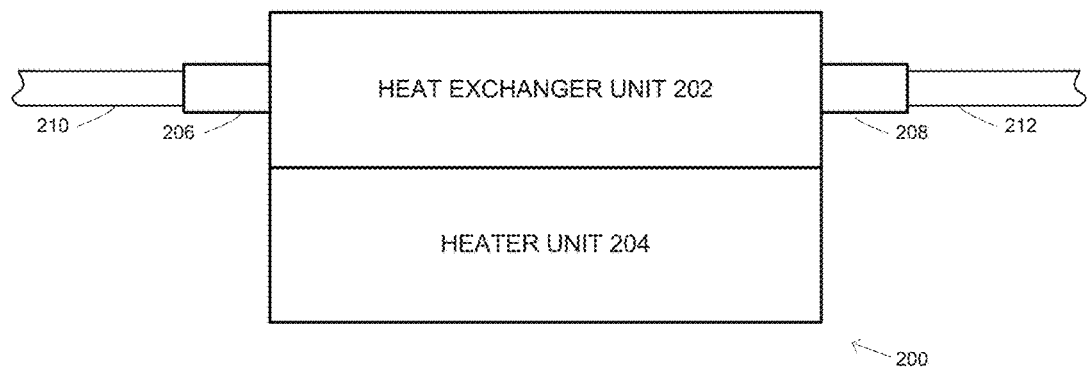
FIG. 2 is a schematic of the fluid warming system as used in FIG. 1.

FIG. 2 is a schematic of the fluid warming system as used in FIG. 1. The fluid warming system 200 of the present embodiment includes a heat exchanger unit 202 and a heater unit 204. The heat exchanger unit 202 includes an inlet 206 and an outlet 208 for attachment to a first IV line 210 and second IV line 212 respectively. An appropriate valve or seal (not shown) is provided on the inlet 206 and outlet 208. In use, the heat exchanger unit 202 is attached to the heater unit 204 to permit heat transfer between the two. The provision of a separate heat exchanger unit, typically in the form of a disposable cassette (see below), can improve the hygiene of the system and can reduce costs by allowing the most expensive part of the warming system to be (re)used indefinitely. In alternative embodiments, the heat exchanger unit 202 may, for example, be integral to the heater unit 204, and other variations are of course possible.

Figure 3:
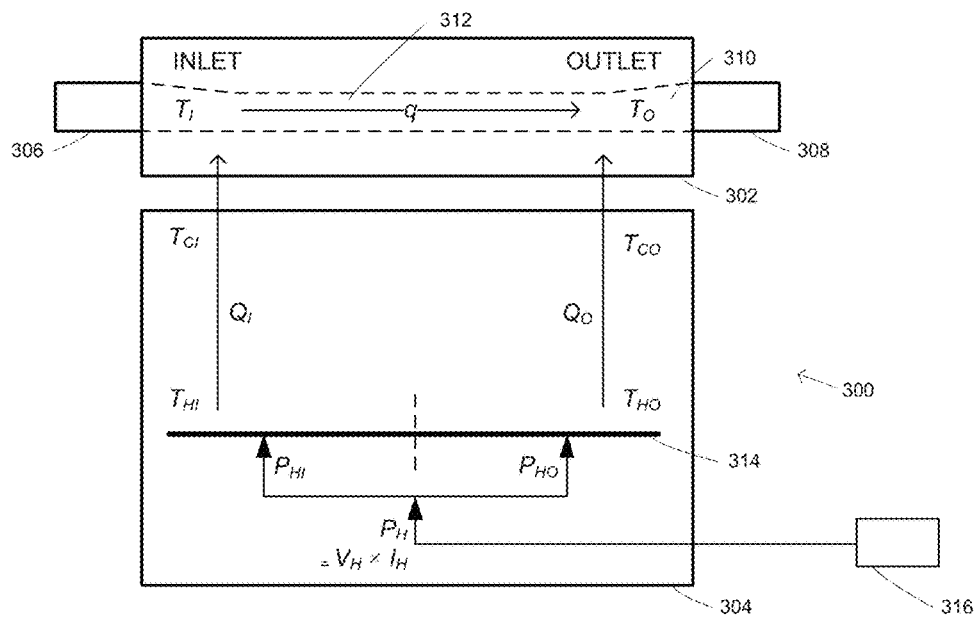
FIG. 3 is a schematic of a heater unit and heat exchanger unit forming part of the fluid warming system of FIG. 2.

FIG. 3 is a schematic of a heater unit and heat exchanger unit forming part of the fluid warming system of FIG. 2. As before, the warming system 300 includes a heat exchanger unit (a disposable cassette, for example) 302 and a heater unit 304. The heat exchanger unit 302 includes an inlet 306 and outlet 308, and also shown is an internal fluid channel 310 running between the inlet and outlet. A significant portion 312 of the channel 310 has a shallow, wide, planar shape (in contrast to the typically round cross-section of an IV line) in order to maximise heat transfer with the heater unit in a minimum amount of time. Within the heater unit, a heater element 314 is controlled by a controller unit 316 in order to heat the fluid passing through the channel 310 and in particular the specially shaped portion 312.

In the system 300, the controller 316 provides a particular electrical power $P_H$ (derivable from the product of the applied heater voltage $V_H$ and heater current $I_H$) to the heater element 314, causing a heat flux to flow between the heater element 314 and fluid within the channel 310. In the present embodiment, the heater element is divided into an inlet heater sub-element and an outlet heater sub-element and the electrical power $P_H$ is divided into an inlet power $P_{HI}$ and an outlet power $P_{HO}$. The power is supplied in a ratio of 3:2 in favour of the inlet, whereby $P_{HI}=0.6\ P_H$ and $P_{HO}=0.4\ P_H$. Different ratios, sub-division shapes and locations and number of sub-divisions are of course possible. In a simplified variant, only a single heater element is provided with a single supplied power $P_H$.

Two areas of particular interest are the heater inlet and heater outlet. At the inlet (or rather, in close thermal proximity), a heat flux $Q_I$ is created by the differential between the heater temperature $T_{HI}$ and the fluid temperature $T_I$. The same flux flows at all points between the heater element 314 and fluid at the inlet, including at the point where the heat exchanger unit (cassette) contacts the surface of the heater unit, having a contact temperature $T_{CI}$. A corresponding (not necessarily identical) heat flux $Q_O$ exists between the heater element 314 and the fluid at the outlet 308 of the system, driven by the temperature differential between heater temperature $T_{HO}$ and fluid temperature $T_O$ at the outlet, and with an associated contact temperature $T_{CO}$ between the two. The total heat flux passing from the heating element 314 to the fluid at a particular fluid flow rate q causes the temperature increase in the fluid from $T_I$ to $T_O$. The heat fluxes $Q_I$, $Q_O$, heater temperatures $T_{HI}$, $T_{HO}$, contact temperatures $T_{CI}$, $T_{CO}$ within the heater unit 304, fluid flow rate q, and fluid temperatures $T_I$, $T_O$ are thus interrelated.

In the present embodiment, the materials and structure of the heat exchanger unit and the heater unit are selected so as to allow efficient heat transfer and to allow meaningful and useful contact temperature measurements, as will be explained in more detail below.

Figure 4:
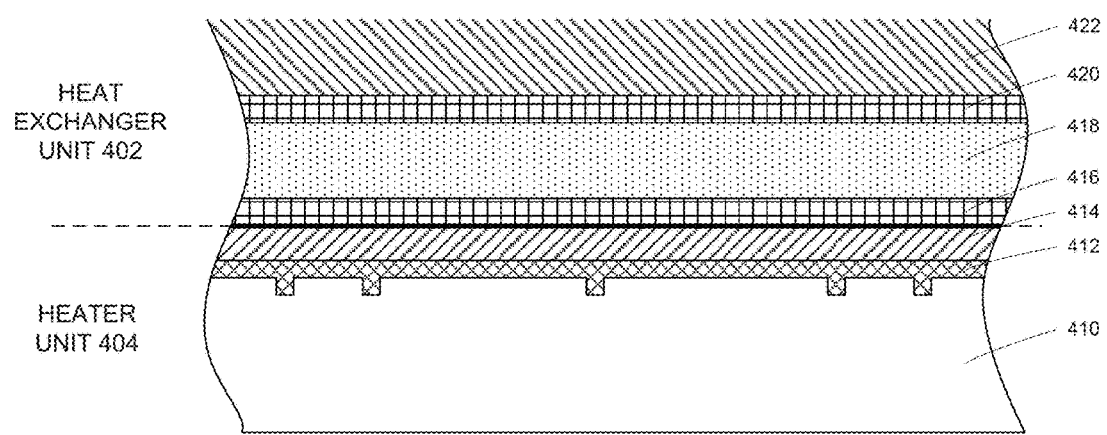
FIG. 4 is a schematic showing different layers of material forming part of the heater unit and heat exchanger unit of FIG. 3 when assembled.

FIG. 4 is a schematic showing different layers of material in one embodiment of the heater unit and heat exchanger unit of FIG. 3. The figure is not to scale and is at least partially exaggerated on the vertical axis. In the figure the heat exchanger unit 202 and heater unit 404 are shown in the engaged configuration (as in use). In the heater unit 404, a foam layer 410 underlies a flex heater 412 which is mounted on a circuit board (not shown). A layer 414 of a thermally conductive but electrically insulating membrane covers the heater 412 to provide protection from environmental damage and electrical short circuit and the like. The heat exchanger unit 402 is coupled to the membrane layer 412 of the heater unit 404 by a parylene coating 416 (or suitable alternative) which covers a relatively thick layer 418 (for structural stiffness) of aluminium, which is separated from the fluid 422 in the fluid channel by another parylene coating 420. Any of the materials mentioned above may of course be replaced by any suitable alternative having appropriate thermal or electrical conductivity, structural stiffness and/or suitability for use in a medical or other setting.

In more detail, in the present embodiment, the membrane layer 414 is formed from a Kapton® (polyimide) sheet, and the heater layer 412 is formed from another Kapton® (polyimide) sheet with copper tracks laid thereon. A conductive paste/coating is provided between the two Kapton® layers 412, 414 but in variants of the present embodiment a thermally conductive phase change material may be provided, or both layers 412, 414 may be replaced by a single thin foil heater with an electrically insulative layer overlaid thereon. Other variants may of course be possible providing they satisfy the requirements of high thermal conductivity, heat resistance and electrical insulation between the heater element and the exposed heating surface of the heater unit. A silicon foam is used for the foam layer 410, but other materials may be provided which have low compression set and high heat resistance properties. Another variant using springs is possible, for example.

Figure 5:
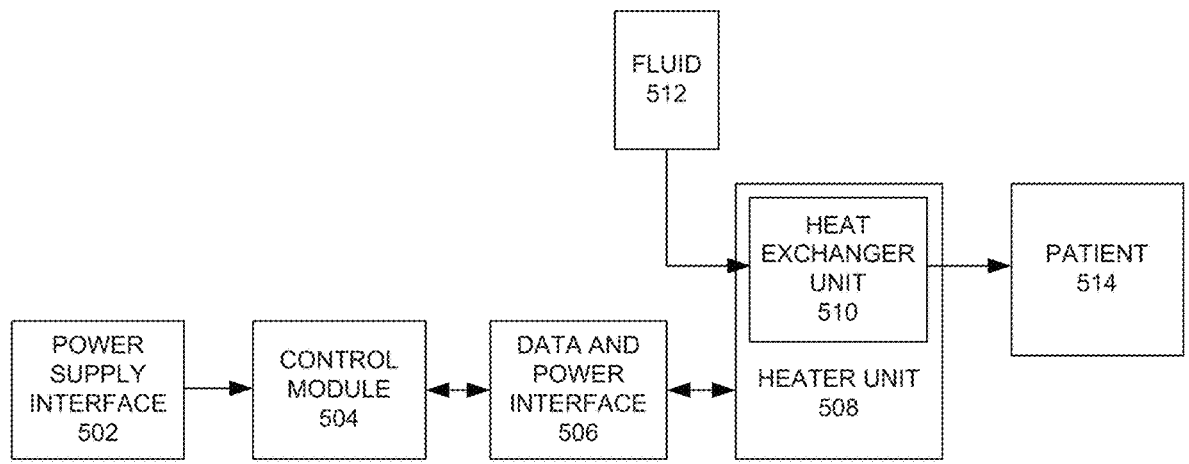
FIG. 5 is a schematic of the warming system of FIG. 2 in more detail.

FIG. 5 is a schematic of the warming system of FIG. 2 in more detail. FIG. 5 shows a power supply interface 502, control module 504, data and power interface 506, heater unit 508 with heat exchanger unit 510 installed, the intravenous fluid 512 and the patient 514 receiving the fluid. The system is divided into two parts: a generally stationary part (typically in the form of a docking cradle) including the power supply, heating control electronics and main user interface, and a transportable part containing the heating element and holding the disposable chamber (heat exchange unit). The control module is intended to be attached to a fluid pole, directly underneath the fluid bag, or to a bed rail, though other alternatives are possible. The heater unit is usually intended to lie beside a patient in bed, or to be attached to the patient's bed sheets or bed rail. The control module typically has a mains inlet and is connected to a wall socket via a power cable (not shown). The control module and heater unit are connected to each other by means of a power and data cable.

The control module offers the possibility to operate the system through a simple user interface. It controls the heating circuitry in order to regulate the heater power in the heater unit. It receives temperature information from the heater unit and notifies the operator of alarm situations. An independent safety circuit in the heater unit prevents the heater from over-heating the fluid. The heater unit decides if some alarm conditions are present and sends this information to the control module.

Figure 6A:
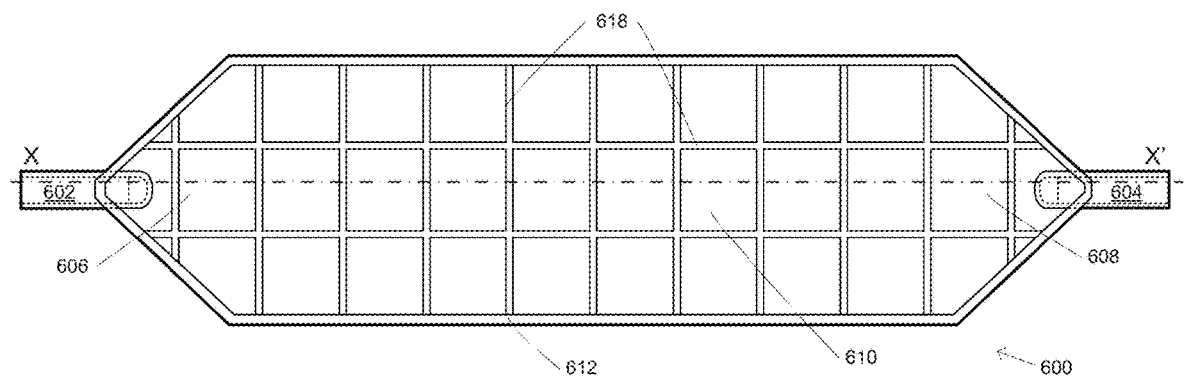
FIGS. 6A, 6B and 6C are schematic illustrations of the heater exchanger unit of a specific embodiment of the fluid warming system of FIG. 2.
Figure 6B:
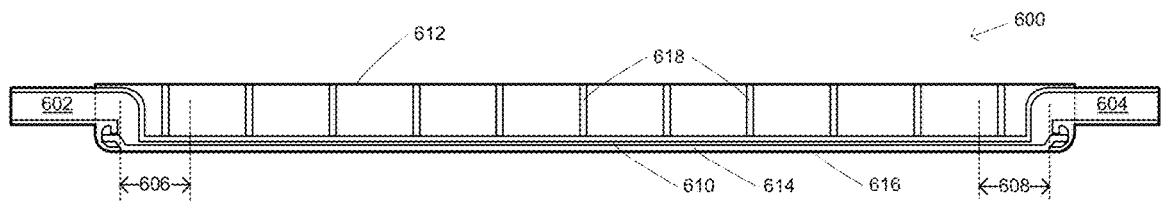
Figure 6C:
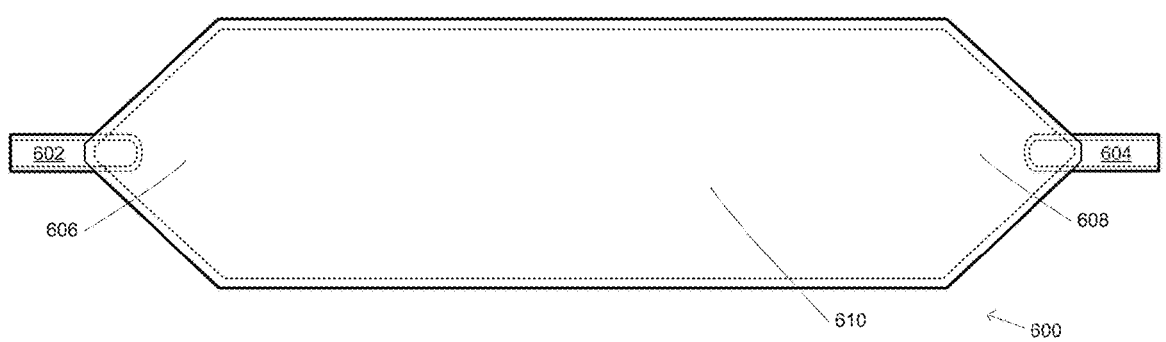

FIGS. 6A, 6B and 6C are schematic illustrations (not to scale or necessarily complete or accurate in every detail) of the heat exchanger unit of a specific embodiment of the fluid warming system of FIG. 2. The heat exchanger unit 600 is provided in the form of a disposable cassette of mostly plastic construction (for sufficient rigidity at relatively low cost and little weight) with the bottom portion having a construction essentially as described above in relation to FIG. 4.

An inlet 602 and outlet 604 connector are shown, having a corresponding inlet portion 606 and outlet portion 608 of the fluid channel where it first makes relatively good thermal contact with the heater element. Sealing elements are provided, cooperating also with a plastic support structure 612, to ensure that the fluid channel 610 and the above-described layers 614 of parylene and aluminium remain well-bonded and in good thermal contact. At the base of the heat exchanger unit 600 there is provided a uniform flat surface 616 for making a good thermal contact with the heater unit. Interlocking vertical plastic webs 618 provide additional rigidity and strength.

Figure 7A:
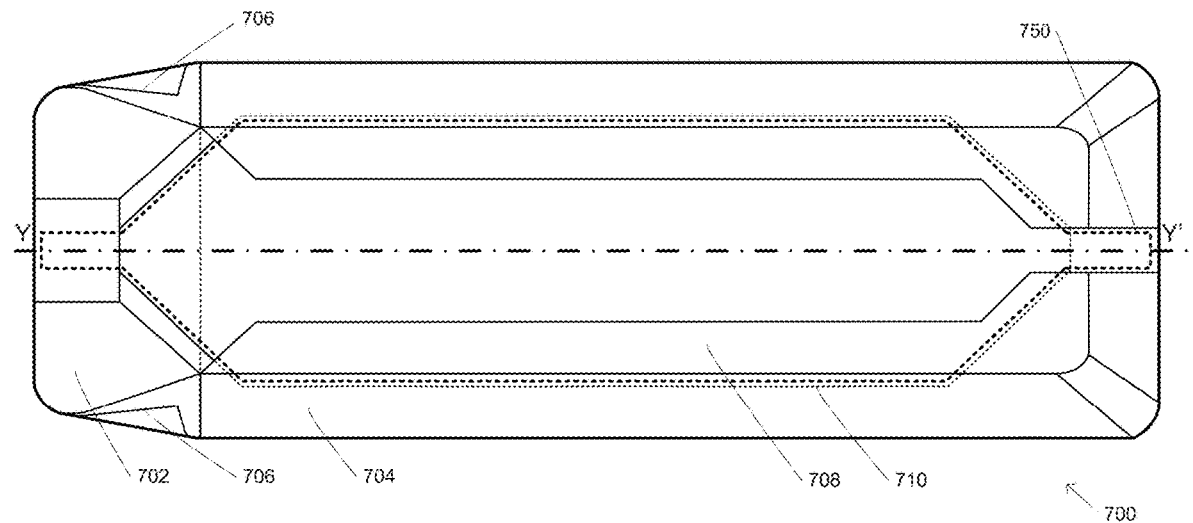
FIGS. 7A, 7B and 7C are schematic illustrations of the heater unit of a specific embodiment of the fluid warming system of FIG. 2.
Figure 7B:
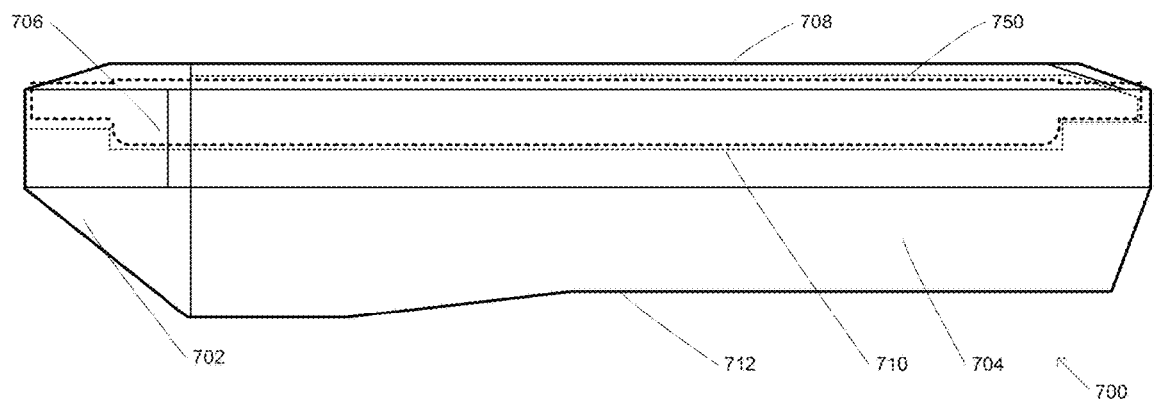
Figure 7C:
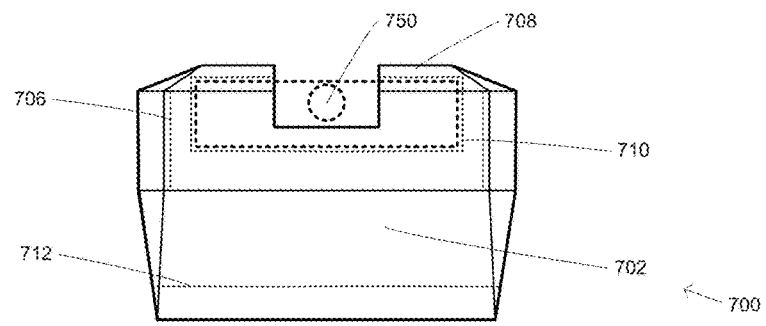

FIGS. 7A, 7B and 7C are schematic illustrations (not to scale or necessarily complete or accurate in every detail) of the heater unit of FIG. 3, suitable for use with the heat exchanger unit described above in relation to FIGS. 6A-C. The heater unit 700 of this embodiment includes a fixed first part 702 for receiving a heat exchanger unit (disposable cassette) as aforementioned and a slideably extendible second part 704 which surrounds most of the length of the first part 702 and locks the cassette in place when in use, as will be described in more detail below. A set of internally-disposed ribs (not shown) perform the function of guiding the slider and locking it into the fully open position. A heater element and control electronics (not shown) form part of the first, fixed part 702. The warmer may be battery-powered (not shown) or function using external power (for example from mains power with appropriate adaptor, not shown, or any appropriate AC or DC source), or both. Battery-powered versions may be particularly suitable for emergency or on-site use, for example, and mains-powered versions may be more suitable for general hospital use and the like.

A hand-grip 706 is provided at the fixed end in the form of a partial indentation in the body of the heater unit. This allows the heater unit 700 to be firmly grasped or clamped at the end of the fixed portion 702 while the sliding portion 704 is moved. The top 708 of the sliding portion is flush with the top of the heat exchanger unit/cassette 750 (shown in outline only in FIGS. 7A-C), when it is present, and prevents the cassette 750 moving out of alignment when the wedge and plunger system (not shown) is activated. The fixed portion 702 of the heater unit 700 includes a recess 710 for receiving the disposable cassette 750 for ease of insertion and retention. At the bottom of the heater unit 700, the lower surface tapers up to a raised surface 712. The purpose of the taper will be explained below in relation to the wedge and plunger (not shown).

In a variant of the present embodiment, ribs (not shown) may be provided on the sliding portion 704 for ergonomic reasons and to provide extra structural strength and resistance to bending moments. Metal reinforcement bars may be provided in addition to or as an alternative to the ribs.

In alternative embodiments a rack and pinion system or a lever mechanism replace the sliding mechanism. Other variants are of course possible.

Figure 8A:
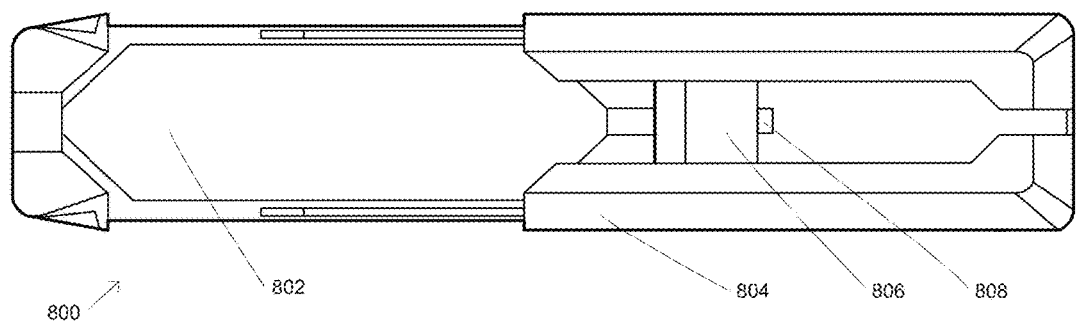
FIGS. 8A, 8B and 8C are schematics illustrating the insertion of the heat exchanger unit of FIGS. 6A-6C into the heater unit of FIGS. 7A-7C.
Figure 8B:
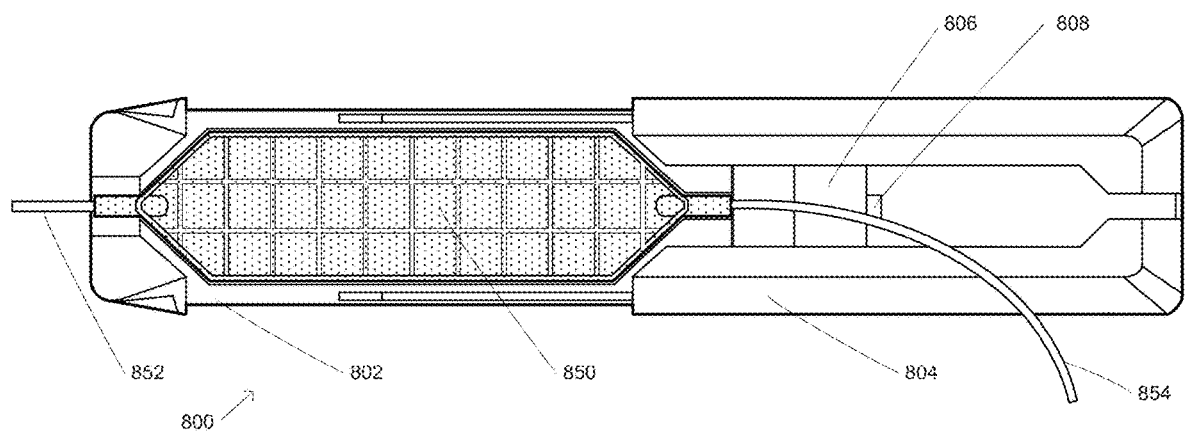
Figure 8C:
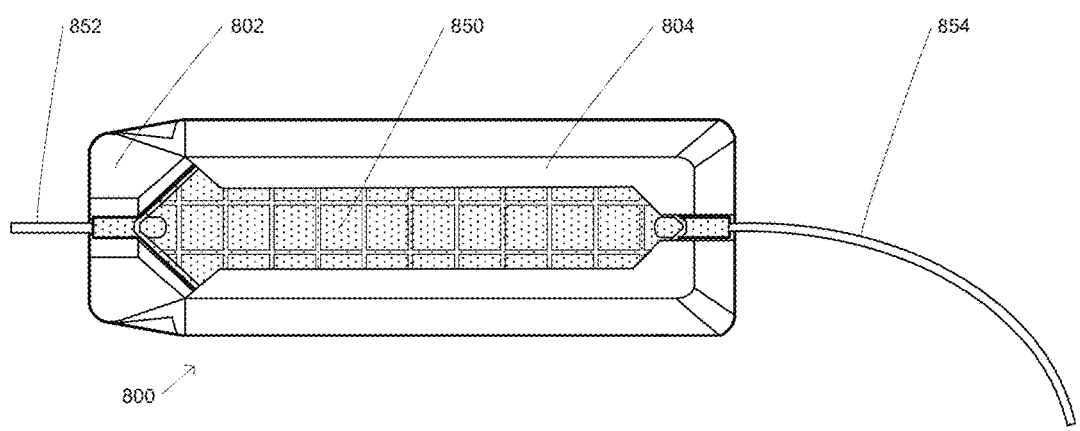

FIGS. 8A, 8B and 8C are schematics illustrating the insertion of the heat exchanger unit of FIGS. 6A-C into the heater unit of FIGS. 7A-C.

In FIG. 8A, the heater unit 800 is shown empty and partially extended, prior to insertion of a cassette (heat exchanger unit). The fixed portion 802 and the sliding portion 804 of the heater unit 800 are indicated. Also visible on the lower interior surface of the sliding portion 802 are a wedge 806, whose shape follows the bottom surface of the sliding portion, and a small depression 808 providing a run-up section for a plunger (not shown) which causes compression of the heating element(s) against the heat exchange unit, as shown n FIG. 8C.

In FIG. 8B, a cassette 850 is shown loaded into the heater unit 800. The cassette/transport unit 850 is shown with IV lines 852, 854 attached to the inlet and outlet respectively.

In FIG. 8C, the heater unit 800 is closed, causing the cassette 850 to be retained, sandwiched between the bottom surface of the top of the sliding portion 802 and a top surface in the recessed area of the fixed portion of the heater unit 800. Again the IV lines 852, 854 are shown. A catch (not shown) is provided to lock the device in the closed position, but other appropriate mechanisms or arrangements are of course possible.

Figure 9:
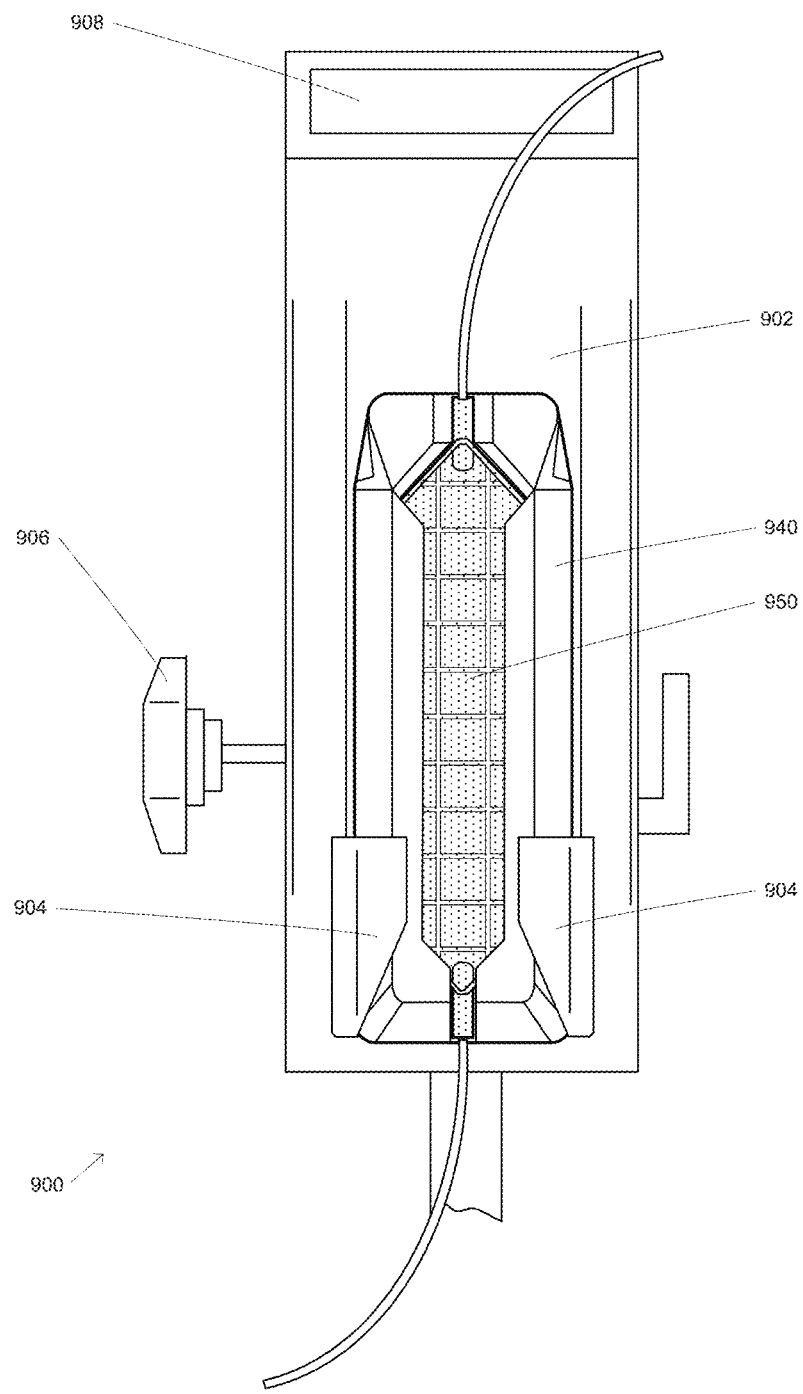
FIG. 9 is an illustration of the insertion of the heater unit and heat exchanger unit of FIG. 8C inserted into a docking cradle.

FIG. 9 is an illustration of the insertion of the heater unit and heat exchanger unit of FIG. 8C inserted into a docking cradle. The cradle includes a recessed portion 902 for receiving the heater unit 940, in turn including a disposable cassette 950. The cradle 900 also includes arms 904 for restraining the heater unit 940. Adjustment wheel 906 can be turned to clamp the unit 940 in place once it is set up. A set of controls 908 facilitates operation of the heater unit 940 and may incorporate additional controls for controlling the IV operation more generally. Power is supplied to the heater unit 940 via a connector in the cradle (not shown), although in a variant of the present embodiment the heater unit 940 is able to operate on battery power or via mains power provided otherwise.

Figure 10A:
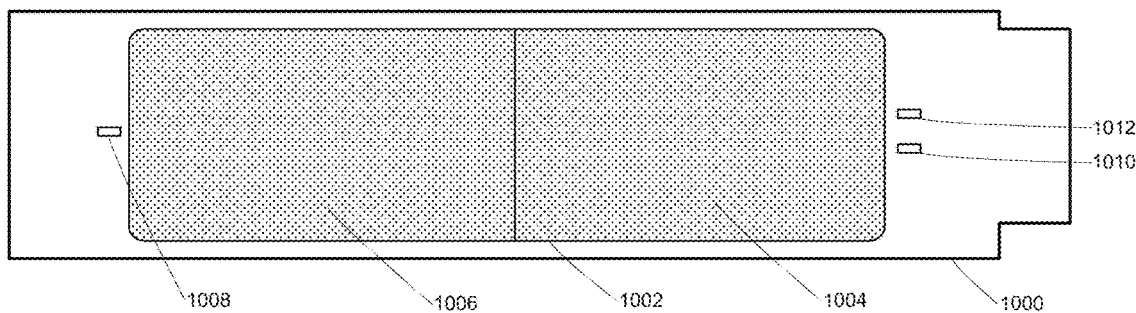
FIGS. 10A and 10B are schematic illustrations of a circuit board inside the heater unit of FIGS. 7A-7C.
Figure 10B:
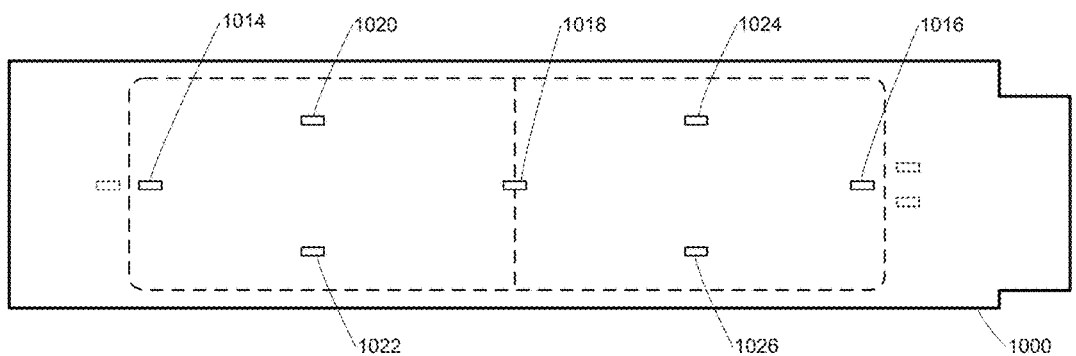

FIGS. 10A and 10B are schematic illustrations of a circuit board inside the heater unit of FIGS. 7A-C. The circuit board in this embodiment includes essentially all heating and control functions (not shown), although additional components may typically be required for interfacing batteries or switching/rectifying/transforming mains power, and the like.

The board 1000 in the present embodiment includes a thin film resistor type heater element 1002, comprising two sub-elements 1004, 1006 on the inlet and outlet side respectively. Each sub-element (or heater area) 1004, 1006 has an identical heater area $A_{heater}$, but different arrangements are possible, including different shapes, numbers and sizes of sub-elements. The heating capacities of the heater areas are 3:2 (inlet:outlet). Thus, ⅗ of the electrical power goes to the inlet part 1006 of the heater and ⅖ of the electrical power goes to the outlet part 1004 of the heater. The reason for providing the different heater areas with different heating capacity was to limit the boundary layer temperatures of the fluid in contact with the Parylene coating on the aluminium; at the inlet of the cassette the fluid is colder and can absorb more heat than near the outlet.

Sensors 1008, 1010, 1012 measure the contact temperatures (including temperatures $T_{CI}$ and $T_{CO}$ of FIG. 3). In particular sensor 1008 measures temperature $T_{CI}$, and sensors 1010, 1012 provide independent (redundant) measurements of temperature $T_{CO}$. Additional temperature sensors 1014, 1016, 1018, 1020, 1022, 1024, 1026 are provided on the reverse of the heater element 1002 for measuring the heater element temperature at different points, including in particular sensors 1014 and 1016 for measuring the heater temperature at the inlet and outlet respectively.

Various systems and subsystems for controlling the application of heater power will now be described.

Figure 11:
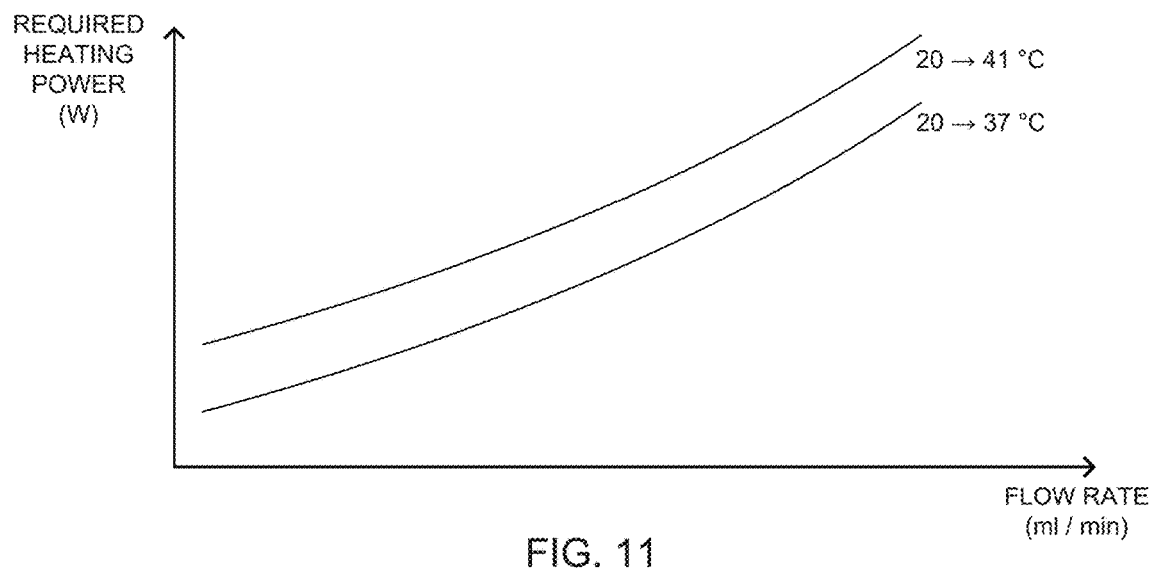
FIG. 11 is a graph illustrating a possible variation of required heating power with increasing fluid flow rate for two different heating scenarios.

FIG. 11 is a graph illustrating a possible variation of required heating power with increasing fluid flow rate for two different heating scenarios. For example, for a given flow rate, which may typically vary between 5 and 100 ml/minute for a medical IV application, increasing the fluid temperature from 20° C. at the inlet to 41° C. at the outlet will require more power than increasing the fluid temperature from the same starting point to 37° C. at the outlet (not surprisingly). For a particular embodiment of heat exchanger unit (cassette) and heater unit, the general relationship between flow rate and required heating power can be determined either by experiment or by theory (and preferably a combination of the two). For example, for the present embodiment, the following values were obtained:

TABLE 1

Heater power required to achieve target outlet fluid temperatures for different flow rates

| Flow rate (ml/min) | Inlet temp (° C.) | Outlet temp (° C.) | Required heater power (W) |
|---|---|---|---|
| 5 | 20 | 37 | 5.9 |
| 5 | 20 | 41 | 7.3 |
| 50 | 20 | 37 | 59.1 |
| 50 | 20 | 41 | 73 |
| 100 | 20 | 37 | 118.2 |
| 100 | 20 | 41 | 146 |

In view of the above it is theoretically possible, though unsafe, to control the heater element to achieve a target fluid temperature without any knowledge or fluid, heater or contact temperatures, for example using a direct measurement of flow rate of the fluid, and an assumption of initial fluid conditions and temperature. However, it is undesirable to have direct measurements in-fluid as this poses several problems, including potential contamination but also the unreliability of moving parts, and so on.

Figure 12:
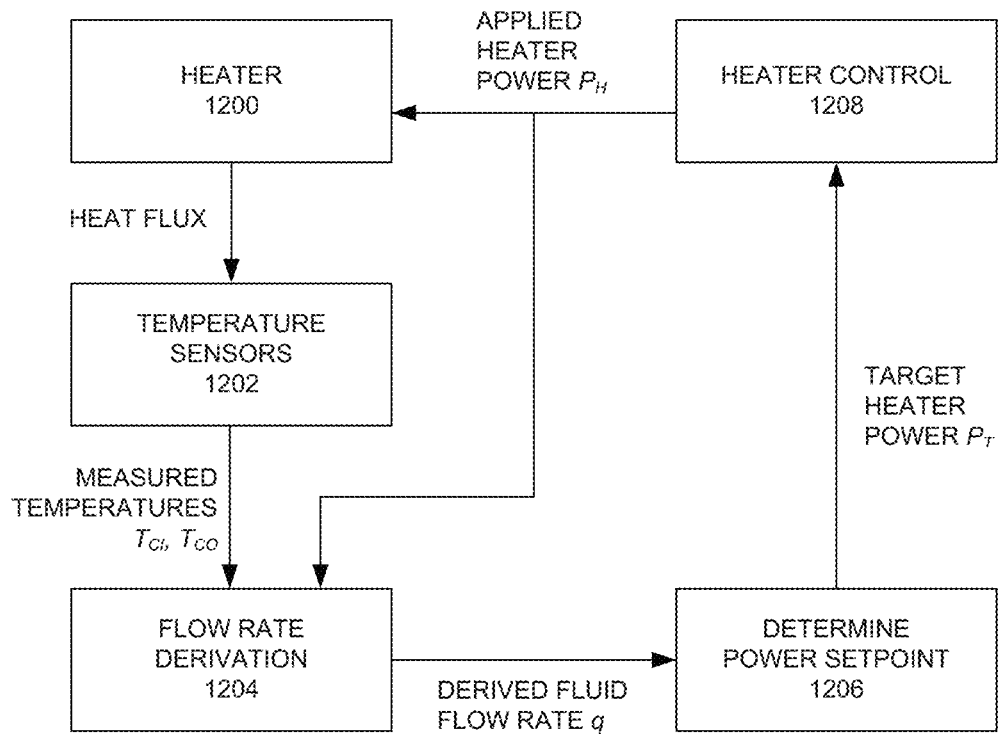
FIG. 12 is an overview of a basic control system for the fluid warming system of FIG. 2.

A control system will now be described in more detail. FIG. 12 is an overview of a basic control system for the fluid warming system of FIG. 2. The heater element 1200 as previously described causes heat to flow, affecting the temperature within the heater unit and heat exchanger unit (cassette). The temperature is recorded by sensors 1202 in the heater unit, to gain a reasonable approximation of the contact temperature at the inlet and outlet (or otherwise, though it is desirable to measure at the extremes of the flow to reduce measurement errors and the like). The measured temperatures (including $T_{CI}$, $T_{CO}$) are used to derive a flow rate q of the fluid, as will shortly be explained, although in practice (and as noted above with regard to FIGS. 10A and 10B), duplicate outlet measurements are used and processed independently to provide redundancy and fail-safe verification, so there are provided additional values $T_O'$, $T_{HO}'$ and $T_{CO}'$ corresponding to the second outlet contact temperature sensor. The derived fluid flow rate q is then used to select 1206 a power set-point (desired heater power $P_T$) for use by the heater control circuit 1208, which controls the power $P_H$ applied to the heater 1200. The selection of a target heater power $P_T$ may for example make use of a predetermined relationship as illustrated in FIG. 11 or Table 1 above.

Figure 13:
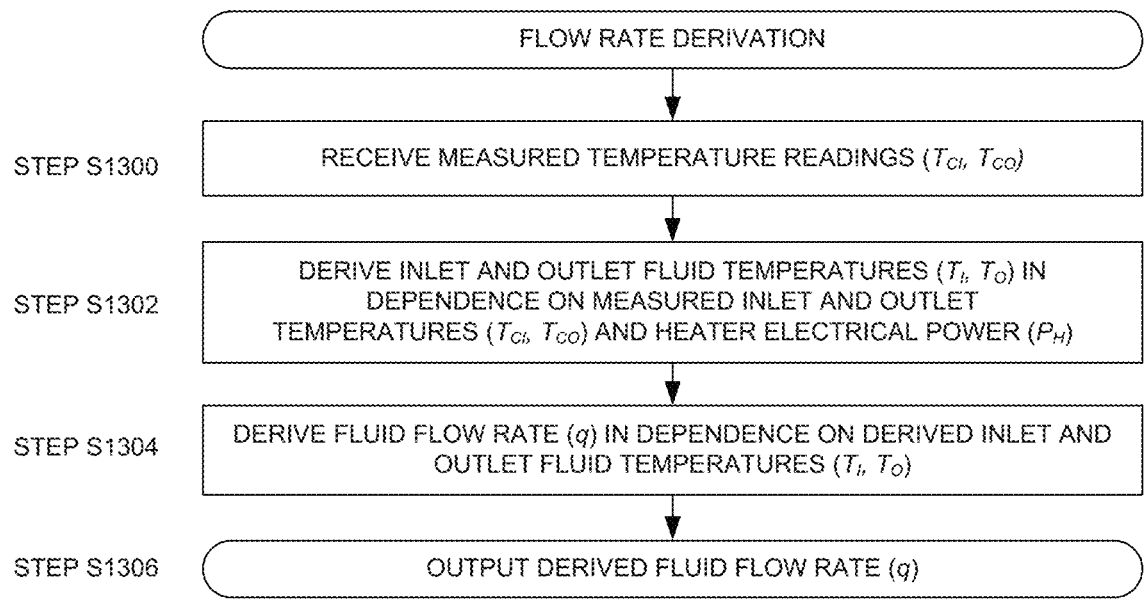
FIG. 13 is a flow chart illustrating the derivation of fluid flow rate in the fluid warming system of FIG. 2.

FIG. 13 is a flow chart illustrating a preferred derivation of fluid flow rate from input temperature measurements in the fluid warming system of FIG. 2, and as may be used in the above scheme. First temperatures are measured (step S1300) relating to the contact temperatures proximate to the inlet and outlet of the heat exchanger unit (specifically the inlet and outlet portions of the channel in good thermal contact with the heater unit). Then (step S1302), inlet and outlet fluid temperatures ($T_I$, $T_O$) are derived from the measured temperatures ($T_{CI}$, $T_{CO}$), as explained in more detail below. Finally a fluid flow rate (q) is derived (step S1304) from the derived inlet and outlet fluid temperatures ($T_I$, $T_O$), and the flow rate is output (step S1306).

The derivations mentioned above will be described in more detail below, with reference to the following constants and pseudo-constants, which may or may not be required in any particular embodiment:

TABLE 2

Constants used in the control system of the specific embodiment

| Constant | Description | Example Values |
|---|---|---|
| $A_H$ | Total contact area between heater and heat exchanger unit [m²] | 0.00162 |
| $A_{HI}$ | Contact area between inlet heater sub-element and heat exchanger unit [m²] | 0.00081 |
| $A_{HO}$ | Contact area between outlet heater sub-element and heat exchanger unit [m²] | 0.00081 |
| pf | Proportion of electric heater output converted to theoretical heat flow to fluid | 0.93 |
| $C_1$ | Amount of joules per minute to heat 1 ml of water by 1 degree C. | 0.069527333 |
| $C_2$ | Embodiment-specific constant determined empirically | 10.52 |
| $C_3$ | Embodiment-specific constant determined empirically | 0.676 |
| $C_{in}$, $C_{out}$ | Embodiment-specific constant determined empirically | |
| $C_{in1}$, $C_{in2}$, $C_{in3}$ | Embodiment-specific constant determined empirically | 1.045, −4.66, 0.088 |
| $C_{out1}$, $C_{out2}$, $C_{out3}$ | Embodiment-specific constant determined empirically | 1.03, −0.387, 0.098 |

It should be noted that some of the above values may not theoretically be constants but can be computed as an average value for a flow rate varying between 5 and 100 ml/min, or similar.

The following input variables are provided in the control system of the main embodiment:

TABLE 3

Input variables used in the control system of the specific embodiment

| Input | Description |
|---|---|
| $T_{CI}$ | Contact temperature at inlet |
| $T_{CO}$ | Contact temperature at outlet |
| $T_{CO}'$ | Contact temperature at outlet (second measurement) |
| $T_{H01}, T_{H02}$ | Heater temperature sensors near inlet |
| $T_{H03}, T_{H04}$ | Heater temperature sensors near outlet |
| $T_{H05}$ | Additional heater temperature sensor measurement |
| $V_H$ | Voltage applied to heater |
| $I_H$ | Current flowing through heater |

The following quantities can be calculated/derived from the input variables and embodiment-specific constants above.

TABLE 4

Calculated/derived variables used in the control system of the specific embodiment

| Input | Description | Formula |
|---|---|---|
| $T_{HI}$ | Heater temperature near inlet | $T_{HI} = (T_{H01} + T_{H02})/2$ |
| $T_{HO}$ | Heater temperature near outlet | $T_{HO} = (T_{H03} + T_{H04})/2$ |
| $T_{HAVG}$ | Average heater temperature | $T_{HAVG} = (T_{H01} + T_{H02} + T_{H03} + T_{H04} + T_{H05})/5$ |
| $P_H$ | Overall power applied to heater | $P_H = P_V \times I_V$ |
| $P_{HI}$ | Power applied to inlet heater element | $P_{HI} = (3/5) P_V \times I_V$ |
| $P_{HO}$ | Power applied to outlet heater element | $P_{HO} = (2/5) P_V \times I_V$ |
| $T_{CAVG}$ | Average contact temperature | $T_{CAVG} = (T_{CI} + T_{CO})/2$ |
| $T_I$ | Derived inlet fluid temperature | $T_I = (C_{IN1} \times T_{CI} + C_{IN2}) - C_{IN3} \times P_H$ |
| $T_O$ | Derived outlet fluid temperature | $T_O = (C_{OUT1} \times T_{CO} + C_{OUT2}) - C_{OUT3} \times P_H$ |
| $T_O'$ | Derived outlet fluid temperature (second/redundant value) | $T_O' = (C_{OUT1} \times T_{CO}' + C_{OUT2}) - C_{OUT3} \times P_H$ |
| $q_{RAW}$ | Uncorrected derived volume flow of fluid | $q_{RAW} = (P_H \times pf)/(C_1 \times (T_O - T_I))$ |
| $q$ | Corrected/final derived flow of fluid ("RC" = RC smoothing filter applied) | $q = RC((q_{RAW} - C_2)/C_3)$ |

The corrected/final derived flow of fluid gin the above table is the flow rate referred to in Step S1306 above.

For one combination of specific heater unit with specific heat transfer unit (cassette), the following constants were determined to be optimal for normal operating conditions:

$$T_I = (1.045 \times T_{CI} - 4.66) - 0.088 \times P_H \quad (1)$$

$$T_O = (1.03 \times T_{CO} - 0.387) - 0.098 \times P_H \quad (2)$$

The constants above were determined using PEMS validation and SigmaPlot® software.

Some alternative control schemes are described below in relation to FIG. 19.

Figure 14:
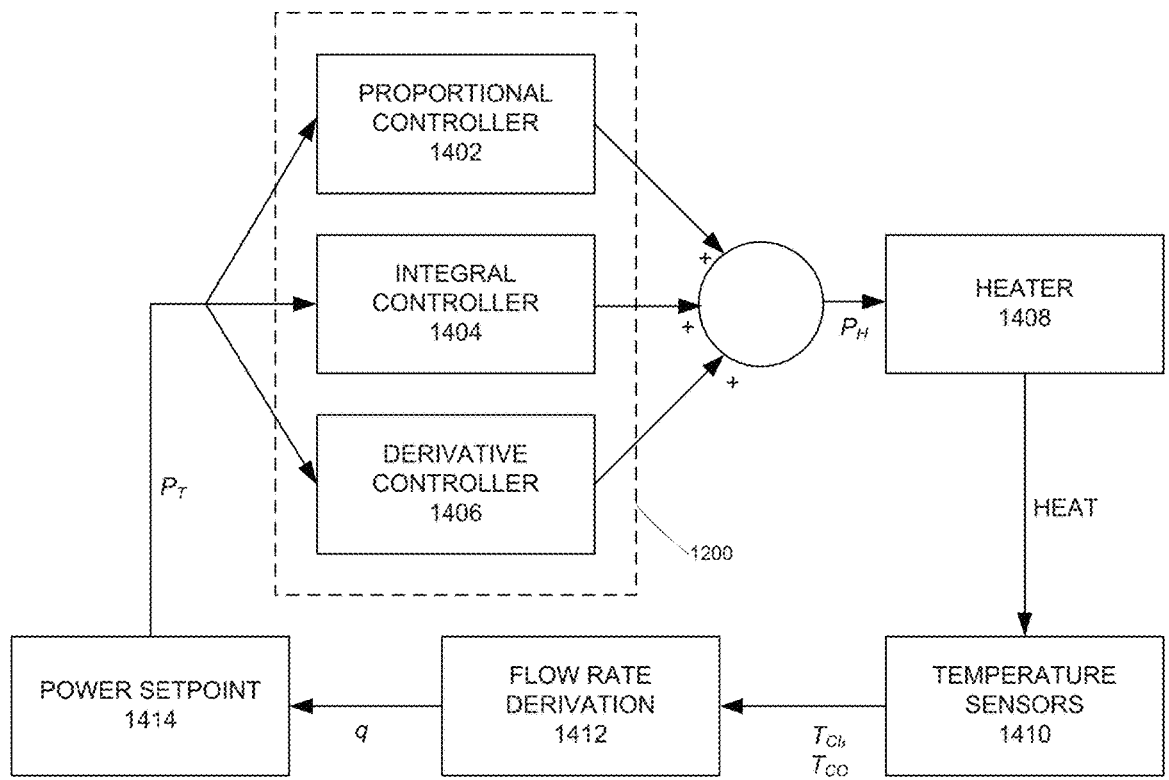
FIG. 14 is a schematic illustrating an example of a more detailed control system based on the control system of FIG. 12.

FIG. 14 is a schematic illustrating an example of a more detailed control system based on the control system of FIG. 12. In this control system, a PID controller 1400, including at least one of a proportional element 1402, integral element 1404 and derivative element 1406, is used to control the power $P_H$ applied to the electrical heater 1408. The heat output by the heater 1408 creates a temperature distribution sensed by sensors 1410, which provide an output to the flow rate derivation process 1412 illustrated in overview in FIG. 11 and described in more detail above in relation to Table 4 and others. The flow rate derivation (and other variables mentioned above) are used to select a target power $P_T$ which is fed back into the PID controller 1400. Appropriate settings for the PID controller can be determined theoretically and empirically as appropriate. Additional control steps may also be provided to provide a model of the plant comprising the particular geometry and configuration of the heater unit and heat exchanger unit.

The heating process is started when the heater unit is closed and a heat exchange unit (disposable cassette) is detected, as will be explained in more detail below in relation to FIGS. 26A and 26B. During the heating process, a number of checks are (near) continuously performed to ensure safety under various circumstances. As part of the process, the controller calculates the power currently used for heating, and calculates the temperature and flow rate of the fluid, as described above. The controller then determines if the fluid temperature is steady (not significantly increasing or decreasing). Initially the heater controller controls the power in such a way as to achieve a stable heat exchange unit (cassette) temperature of 40 degrees C. at the fluid outlet sensor (for these purposes, 40 degrees C. heat exchange unit temperature is considered safe).

For determination of the set point needed to reach an end of line (outlet) temperature of 39 degrees C., a good estimation of the fluid flow rate and incoming fluid temperature is important. To do this, a calculation is made as described above, based on the heat exchange unit temperatures at the fluid inlet and outlet, and the power delivered to the heater. A stable output temperature has to be realised. When the output temperature is stable, a new set point value for the heater control is calculated. This event is called a 'snapshot'. A snapshot is taken if (1) a rising edge is seen on a PID steady indicator (meaning the temperature has transitioned from unsteady to steady), or (2) PID steady is true and the last snapshot was taken more than 5 seconds previously, or (3) the last snapshot was taken more than 20 seconds previously. The set point temperature is then determined, and the PID controller is adjusted to heat up or cool down to the new set point, and the heater is activated.

Figure 15:
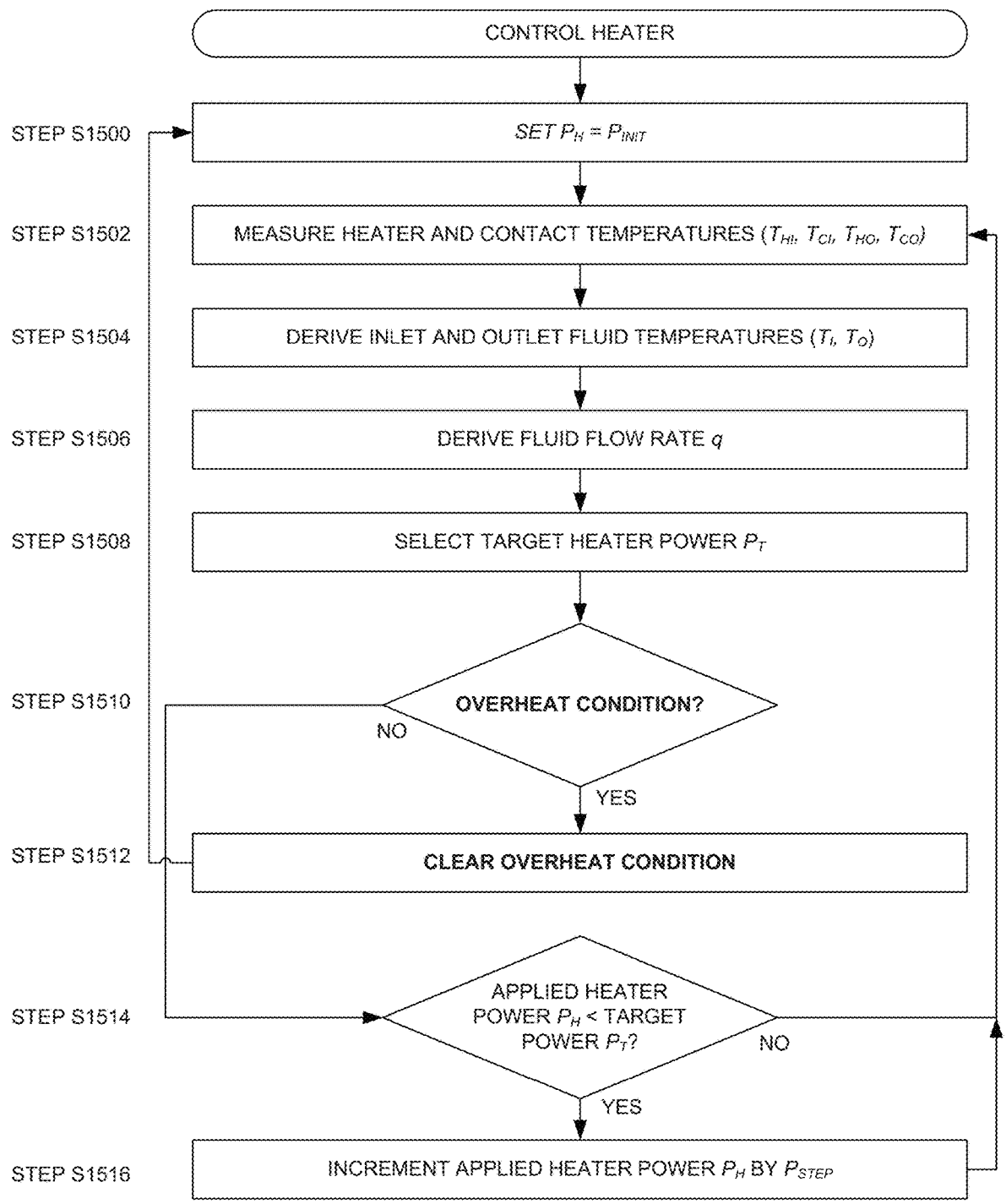
FIG. 15 is a flow chart illustrating a scheme for controlling the heater of the fluid warming system of FIG. 2.

FIG. 15 is a flow chart illustrating a scheme for controlling the heater of the fluid warming system of FIG. 2. This flow chart represents a first type of program which can be used to control the heater unit.

Initially (step S1500) the current heater power $P_H$ is set to an initial value $P_{INIT}$, which may for example be 10 watts (W). The various temperatures are measured (step S1502), fluid temperatures (and, optionally, heat fluxes) derived (step S1504) and fluid flow rate q derived (step S1506) as explained above. A target heater power $P_T$ is selected (step S1508) depending on the flow rate q and the target temperature (for example between 37° C. and 41° C.). At this point in the control loop (step S1510) and/or elsewhere, a test is carried out to check whether the heater unit is overheating, as will be explained in more detail below with reference to FIG. 17. If the unit is overheating, a different mode is entered until the overheating condition is cleared (step S1512, again see below), and then the control loop resets and returns to step S1500. If, on the other hand, there is no overheat condition, if (step S1514) the current heater power $P_H$ is less than the dynamically selected (in step S1508) target heater power $P_T$, then the current heater power is increased by a fixed amount $P_{STEP}$ (step S1516) and the control loop is restarted at step S1502. An alternative control scheme is outlined below, but the presently described scheme may be altered as appropriate and/or necessary, for example to apply a different and/or dynamically varying increment to the current heater power, and so on.

Figure 16:
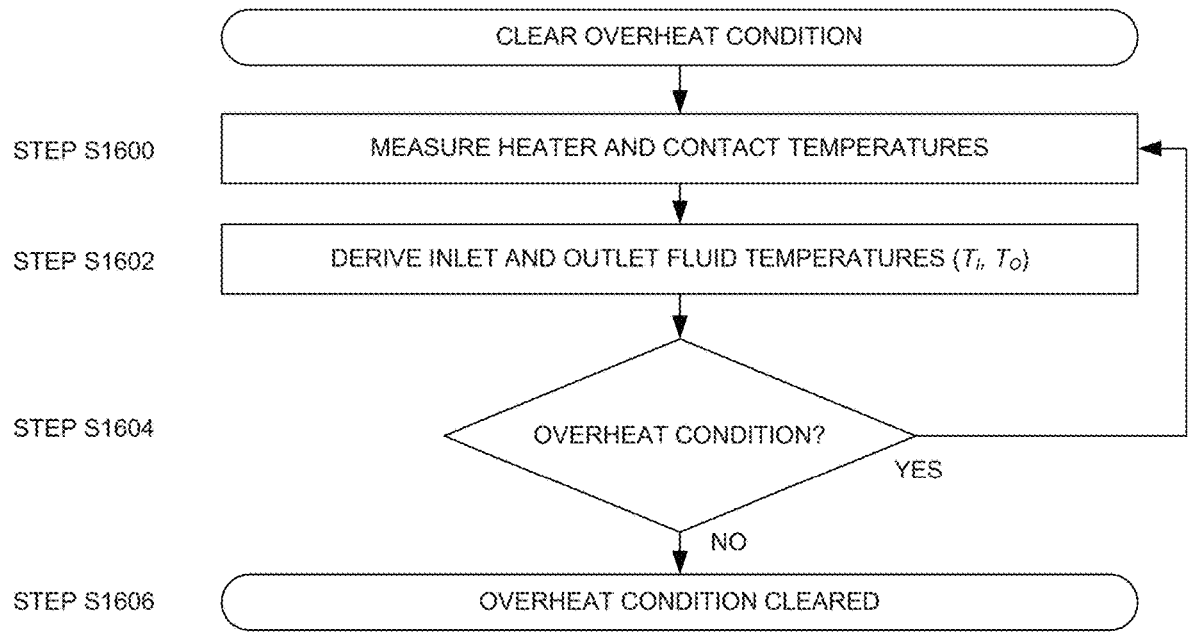
FIG. 16 is a flow chart illustrating a process for clearing an overheat condition, suitable for use in the scheme of FIG. 12.

FIG. 16 is a flow chart illustrating a process for clearing an overheat condition, suitable for use in the scheme of FIG. 15. This may for example represent an operating mode which may be purely conceptual or more clearly demarcated, for example using different processes and the like. In step S1600 the heater and contact temperatures are measured as before. If possible and appropriate (see below), in step S1602 derived fluid temperatures (and optionally also heat fluxes) are derived as before. Overheating is typically defined with reference to the measured and (if possible) derived temperatures, and an appropriate test is carried out in step S1604. If the system is still overheating, the process loops back to step S1600. Otherwise the operating mode terminates and the overheat condition is cleared (step S1606). Derivation of the flow rate q is not normally required, and is omitted in this instance. In fact, during an overheat condition the electrical power is normally turned off, which prevents the determination of essentially all of the derived variables mentioned above (not just the flow rate q which depends on the heater power $P_H$ but also the derivation of heat fluxes and so on, if appropriate, because there is no meaningful heat flux when the heater is disabled). In this mode, with the heater disabled, step S1602 is omitted, and the overheat condition is determined with respect only to directly measured temperatures (in particular contact temperatures $T_{CI}$ and $T_{CO}$).

Figure 17:
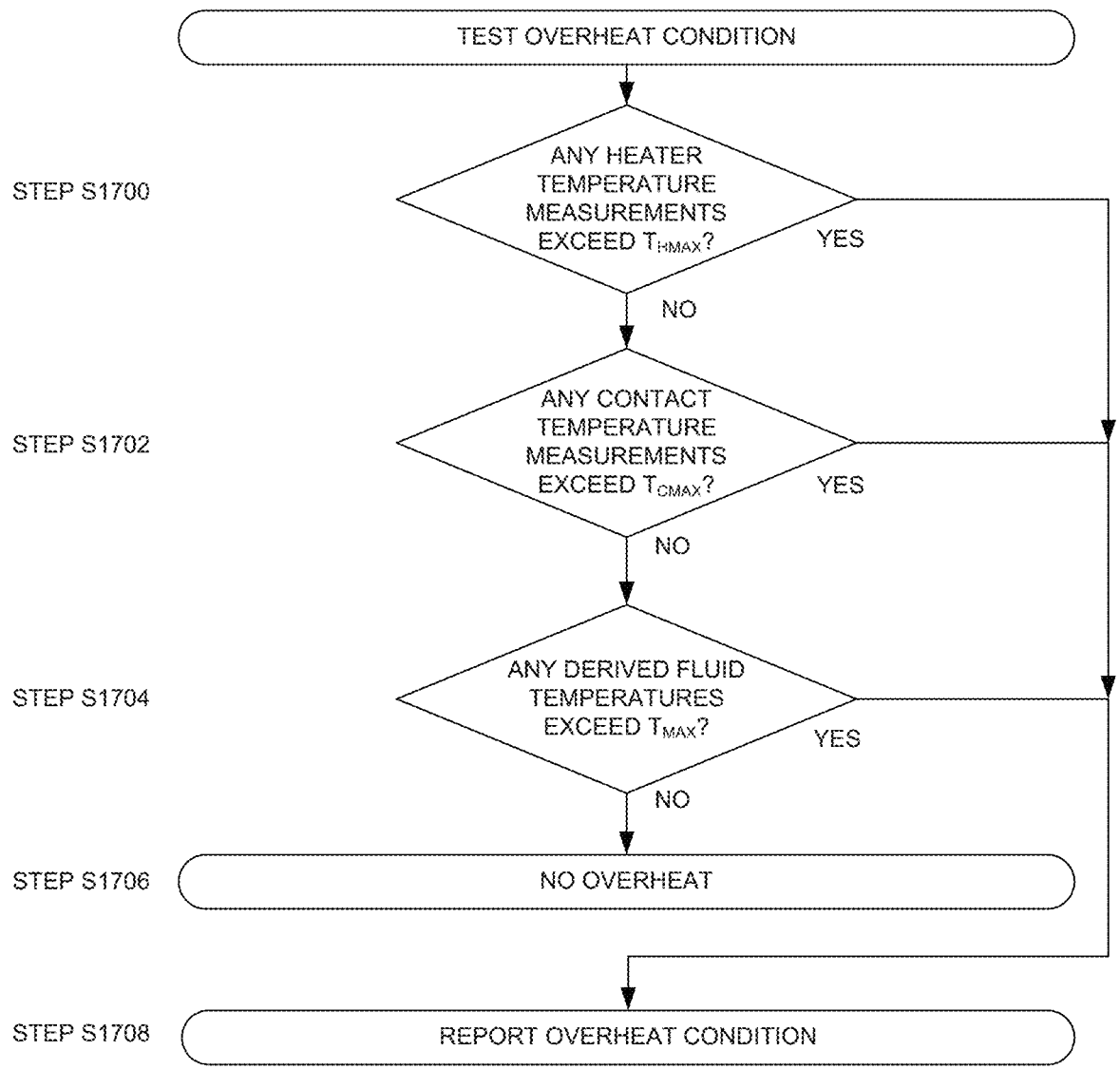
FIG. 17 is a flow chart illustrating a process for testing for an overheat condition, suitable for use in the scheme of FIG. 12.

FIG. 17 is a flow chart illustrating a process for testing for an overheat condition, suitable for use in the flow charts of FIGS. 15 and 16. In step S1700 a test is made as to whether any heater temperature measurements (such as $T_{HI}$, $T_{HO}$, or $T_{H01}$, $T_{H02}$, $T_{H03}$, $T_{H04}$, $T_{H05}$ mentioned above) exceed a predefined (or dynamically derived) maximum temperature $T_{HMAX}$, which in the present embodiment is set to 55° C. (though an appropriate value will depend on the chosen structure, geometry and materials for a particular embodiment). If the temperature limit is exceeded (or, optionally, equalled), then the overheat condition is indicated (step S1708). Otherwise, in the next test (step S1702) a test is made as to whether any contact temperature measurements ($T_{CI}$, $T_{CO}$, $T_{CO}'$) exceed a further temperature limit $T_{CMAX}$, which in the present embodiment is chosen to be 52° C. Again, if the test is failed, the overheat condition is indicated (step S1708). Finally, a test is made (if possible and/or appropriate) to see if any derived fluid temperatures ($T_I$, $T_O$) exceed a threshold $T_{MAX}$, which will typically be set to have a particular relation to the currently selected fluid target temperature (which may typically be in the region of 37-41° C.), for example being a fixed offset or a fixed multiple of the current target temperature. $T_{MAX}$ may for example be in the range of 39-43° C. If the temperature is exceeded, the overheat condition is indicated (step S1708), otherwise the test returns without an overheat condition being indicated (step S1706).

In addition to the above, an overheat condition is triggered if the fluid temperature is too high for a particular length of time which is dependent on the temperature. Thus higher temperatures which otherwise fall within the safety margin can be maintained only for limited periods of time, and lower temperatures can be maintained for longer periods of time, as explained below in more detail with reference to FIG. 28. Additional checks are typically made, such as triggering an overheat condition only if the fluid temperature exceeds a certain value (45 degrees centigrade in the present embodiments) and when the heater exceeds a particular current (0.5 A in the present embodiments).

Figure 18:
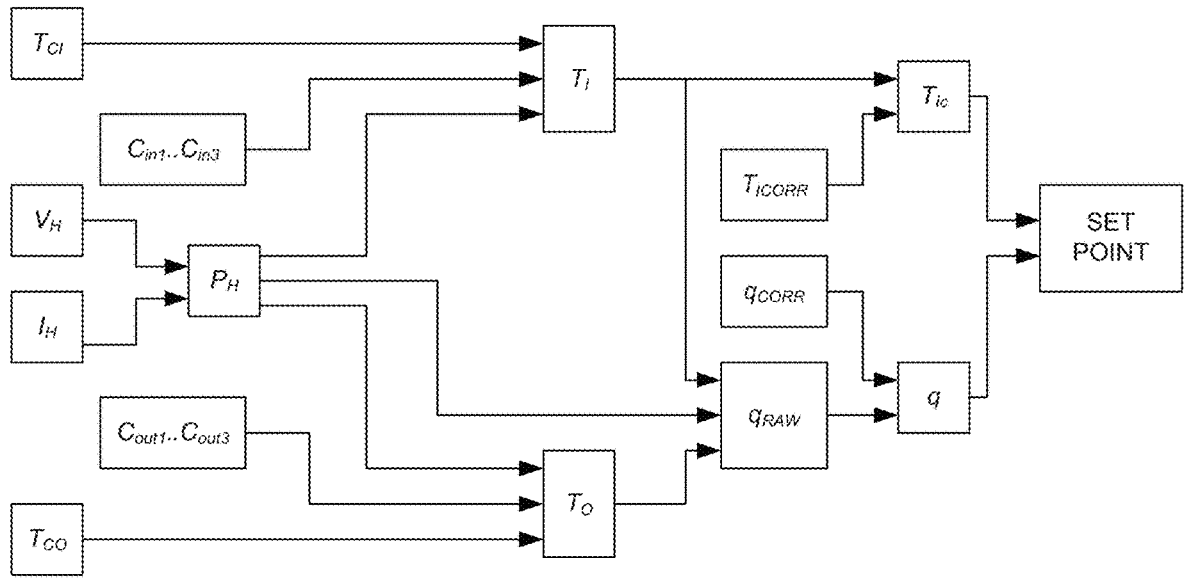
FIG. 18 is a diagram illustrating the data flow and dependencies of the scheme of FIG. 15.

FIG. 18 is a diagram illustrating the data flow and dependencies of the control scheme of FIG. 12. As is explained above in relation to FIG. 13, $T_{CI}$ and $T_{CO}$ are the inlet and outlet contact temperature measurements, as before. $V_H$ and $I_H$ are the voltage and current supplied to the heater elements, from which the overall heater power $P_H$ can be derived. Inlet and outlet fluid temperatures $T_I$, $T_O$ are derived from the contact temperatures and the heater power using the constants $C_{in1}$, $C_{in2}$, $C_{in3}$ and $C_{out1}$, $C_{out2}$, $C_{out3}$ (or any other appropriate constants and/or calibration method). The total heater power $P_H$ and derived inlet and outlet fluid temperatures $T_I$, $T_O$ are then processed as explained above to derive an uncorrected/raw fluid flow rate estimate $q_{RAW}$. An appropriate correction $q_{CORR}$ is applied to generate a refined estimate of fluid flow rate q. Similarly, a correction $T_{ICORR}$ is applied to the inlet temperature estimate $T_I$ to generate a refined estimate $T_{Ic}$ of fluid inlet temperature. The refined estimates of inlet temperature $T_{Ic}$ and fluid flow rate q are then used (for example in conjunction with a required heating power function as illustrated in FIG. 11) to determine an appropriate power setpoint.

Figure 19:
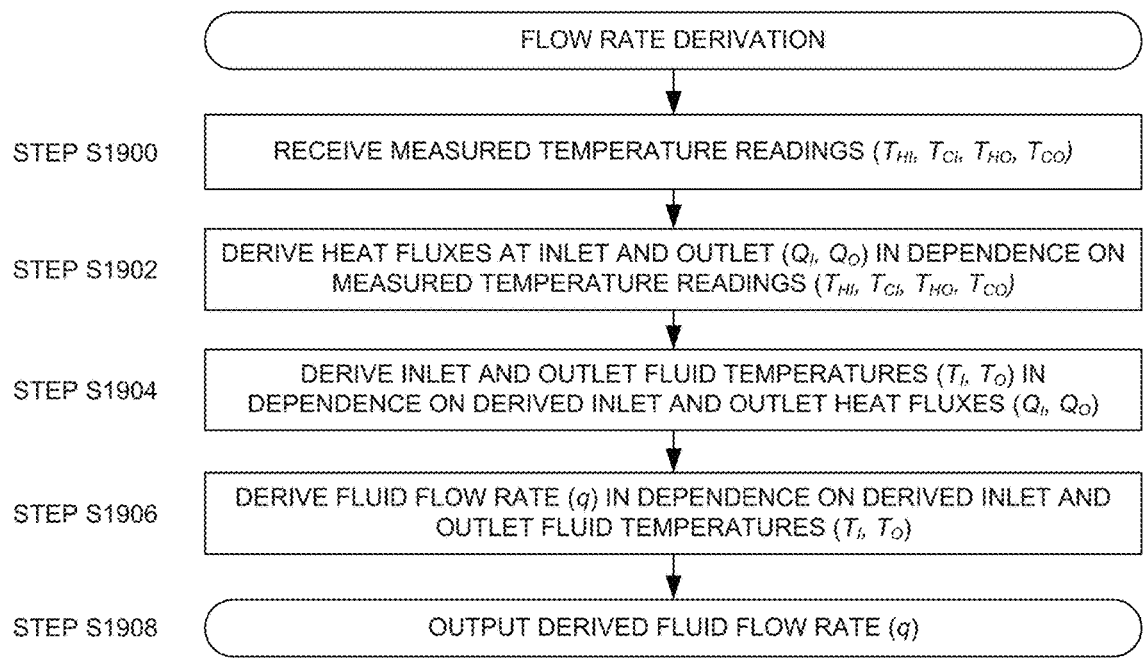
FIG. 19 is a flow chart illustrating an alternative derivation of fluid flow rate from input temperature measurements in the fluid warming system of FIG. 2.

FIG. 19 is a flow chart illustrating an alternative control scheme, including an alternative derivation of fluid flow rate from input temperature measurements in the fluid warming system of FIG. 2. After temperatures are measured (step S1900) relating to the contact and heater temperatures proximate to the inlet and outlet of the heat exchanger unit (specifically the inlet and outlet portions of the channel in good thermal contact with the heater unit), heat fluxes $Q_I$ and $Q_O$ are derived (step S1902) from the contact and heater temperatures proximate to the inlet and outlet of the heat exchanger unit. Next (step S1904), inlet and outlet fluid temperatures ($T_I$, $T_O$) are derived from the heat fluxes $Q_I$ and $Q_O$. Finally (step S1906) a fluid flow rate (q) is derived from the derived inlet and outlet fluid temperatures ($T_I$, $T_O$), and the flow rate is output (step S1908).

In a first version of the alternative control scheme, the following quantities are calculated/derived from the input variables and embodiment-specific constants above.

TABLE 5

Calculated/derived variables used in the control system of a first alternative control scheme

| Input | Description | Formula |
|---|---|---|
| $T_{HI}$ | Heater temperature near inlet | $T_{HI} = (T_{H01} + T_{H02})/2$ |
| $T_{HO}$ | Heater temperature near outlet | $T_{HO} = (T_{H03} + T_{H04})/2$ |
| $T_{HAVG}$ | Average heater temperature | $T_{HAVG} = (T_{H01} + T_{H02} + T_{H03} + T_{H04} + T_{H05})/5$ |
| $P_H$ | Overall power applied to heater | $P_H = P_V \times I_V$ |
| $P_{HI}$ | Power applied to inlet heater element | $P_{HI} = (3/5) P_V \times I_V$ |
| $P_{HO}$ | Power applied to outlet heater element | $P_{HO} = (2/5) P_V \times I_V$ |
| $T_{CAVG}$ | Average contact temperature | $T_{CAVG} = (T_{CI} + T_{CO})/2$ |
| $Q_I$ | Heat flux from heater to heat exchanger unit at inlet | $Q_I = P_{HI}/A_{HI}$ |
| $Q_O$ | Heat flux from heater to heat exchanger unit at outlet | $Q_O = P_{HO}/A_{HO}$ |
| $T_I$ | Derived inlet fluid temperature | $T_I = T_{CI} - (Q_I/K_{in})$ |
| $T_O$ | Derived outlet fluid temperature | $T_O = T_{CO} - (Q_O/k_{out})$ |
| $T_O'$ | Derived outlet fluid temperature (second/redundant value) | $T_O' = T_{CO}' - (Q_O/k_{out})$ |
| $q_{RAW}$ | Uncorrected derived volume flow of fluid | $q_{RAW} = (P_H \times pf)/(C_1 \times (T_O - T_I))$ |
| q | Corrected/final derived flow of fluid ("RC" = RC smoothing filter applied) | $q = RC((q_{RAW} - C_2)/C_3)$ |

It is noted in particular that the derivations for $T_i$ and $T_o$ differ from the main embodiment described above with reference to FIG. 13.

$k_{in}$ and $k_{out}$ are heat transfer coefficients with respect to the inlet and outlet part of the heater, typically derived by experiment, and $T_O'$ is a redundant value for the outlet fluid temperature (which can provide an independent/redundant temperature reading for the safety controller of FIG. 21, for example, discussed below).

Here the derivation of the heat flux from heater to heat exchanger unit is based on the temperature difference between heater and contact temperature sensors at the inlet and outlet. While this derivation is more closely based on the physical processes underlying the heat flux, it will be appreciated that imprecisions in the temperature sensing can create consequential inaccuracies in the estimate.

A second version of the alternative control scheme will now be discussed, which differs from the first version in respect of how the heat fluxes $Q_I$, $Q_O$ (and consequent values) are derived:

TABLE 6

Calculated/derived variables used in the control system of a second alternative control scheme

| | | |
|---|---|---|
| $Q_I$ | Heat flux from heater to heat exchanger unit at inlet | $Q_I = k \times (T_{HI} - T_{CI})$ |
| $Q_O$ | Heat flux from heater to heat exchanger unit at outlet | $Q_O = k \times (T_{HO} - T_{CO})$ |
| $Q_O'$ | Heat flux from heater to heat exchanger unit at outlet (second/redundant value) | $Q_O' = k \times (T_{HO} - T_{CO}')$ |
| $T_I$ | Derived inlet fluid temperature | $T_I = T_{CI} - (Q_I/k_{c-f})$ |
| $T_O$ | Derived outlet fluid temperature | $T_O = T_{CO} - (Q_O/k_{c-f})$ |
| $T_O'$ | Derived outlet fluid temperature (second/redundant value) | $T_O' = T_{CO}' - (Q_O/k_{c-f})$ |
| $q_{RAW}$ | Uncorrected derived volume flow of fluid | $q_{RAW} = (P_H \times pf)/(C_1 \times (T_O - T_I))$ |
| q | Corrected/final derived flow of fluid ("RC" = RC smoothing filter applied) | $q = RC((q_{RAW} - C_2)/C_3)$ |

Alternative formulas can also be used for the derivation of inlet and outlet fluid temperature:

$$T_I = T_{CI} - (P_H \times C_{IN}) \quad (4)$$

$$T_O = T_{CO} - (P_H \times C_{out}) \quad (5)$$

or the following approximation can be used (given small differences between $k_{in}$ and $k_{out}$ mentioned above):

$$T_I = T_{CI} - (Q_I/k_{c-f}) \quad (6)$$

$$T_O = T_{CO} - (Q_O/k_{c-f}) \quad (7)$$

$$T_O' = T_{CO}' - (Q_O/k_{c-f}) \quad (8)$$

Equations (4) and (5) are simplified versions of equations used previously, and have the benefit of simplicity and efficiency, but can be less accurate in some circumstances. Other derivations are of course possible.

The derivation of $k_{c-f}$ and related heat transfer coefficient information is given in the following table:

TABLE 7

Additional constants used in the control system of a second alternative control scheme

| | | |
|---|---|---|
| $k_{h-c}$ | Heat transfer coefficient from heater to cassette (heat exchanger) interface = $(\delta_{hk}/\lambda_{hk}) + (\delta_{hc}/\lambda_{hc}) + (\delta_{hp}/\lambda_{hp}) + (\delta_m/\lambda_m) + (1/\alpha_{m-p})$ [W/m²K] | |
| $k_{c-f}$ | Heat transfer coefficient from cassette (heat exchanger) interface to fluid = $(\delta_{p1}/\lambda_{p1}) + (\delta_{al}/\lambda_{al}) + (\delta_{p2}/\lambda_{p2}) + (1/\alpha_{p-f})$ [W/m²K] | |
| $k_{in}$ | Heat transition coefficient at inlet part of heater [W/m²K] | 3764.811217 |
| $k_{out}$ | Heat transition coefficient at outlet part of heater [W/m²K] | 3774.8581 |
| $\delta_{hk}$ | Heater Kapton layer thickness [m] | |
| $\lambda_{hk}$ | Heater Kapton layer thermal conductivity [W/mK] | |
| $\delta_{hc}$ | Heater copper pattern thickness [m] | |
| $\lambda_{hc}$ | Heater copper pattern thermal conductivity [W/mK] | |
| $\delta_{hp}$ | Heat paste thickness [m] | |
| $\lambda_{hp}$ | Heat paste thermal conductivity [W/mK] | |
| $\delta_m$ | Kapton membrane thickness [m] | |
| $\lambda_m$ | Kapton membrane thermal conductivity [W/mK] | |
| $\alpha_{m-p}$ | Heat transfer coefficient from Kapton membrane to Parylene coating [W/m²K] | |
| $\delta_{p1}$ | Parylene coating on aluminium (outside) thickness [m] | |
| $\lambda_{p1}$ | Parylene coating on aluminium (outside) thermal conductivity [W/mK] | |
| $\delta_{al}$ | Aluminium layer thickness [m] | |
| $\lambda_{al}$ | Aluminium layer thermal conductivity [W/mK] | |
| $\delta_{p2}$ | Parylene coating on aluminium (inside) thickness [m] | |
| $\lambda_{p2}$ | Parylene coating on aluminium (inside) thermal conductivity [W/mK] | |
| $\alpha_{p-f}$ | Heat transfer coefficient from Parylene coating to fluid [W/m²K] | |

The heat transfer coefficient from heater to cassette (heat exchanger) interface $k_{h-c}$ may alternatively be derived dynamically as $$k_{h-c} = P_H/(A_H \times (T_{HAVG} - T_{CAVG})) \quad (3)$$

It usually suffices, however, to treat $k_{h-c}$ as a predetermined constant.

In practice, $k_{h-c}$ and $k_{c-f}$ can be derived by performing a range of fluid inlet temperature and flow rate combination tests, and tweaking the heat transfer coefficients to obtain the highest precision compared to fluid temperatures measured directly in the fluid at the inlet and outlet of the cassette (heat exchanger unit). However, the derived heat transition coefficients are specific for the module they have been derived on. Thicknesses of material layers outside the specific range or usage of other materials of the heater may require other heat transition coefficients.

It is known, for example, that thermal properties of materials can change as temperature varies (that is, the thermal conductivities are functions of the temperature). As another example, the heat transfer coefficient $\alpha_{p-f}$ of the Parylene coating is a function of fluid velocity and temperature. However, compared to the other factors that determine the heat transition coefficient, the heat transfer coefficient of the Parylene coating is so large that the exact value does not influence the result significantly. Therefore, a constant value for the heat transfer coefficient $\alpha_{p-f}$ was used for simplicity.

It will be appreciated that appropriate values of the above constants can be determined empirically and/or by analysis of the relevant materials, structures and geometry of a specific embodiment.

Figure 20:
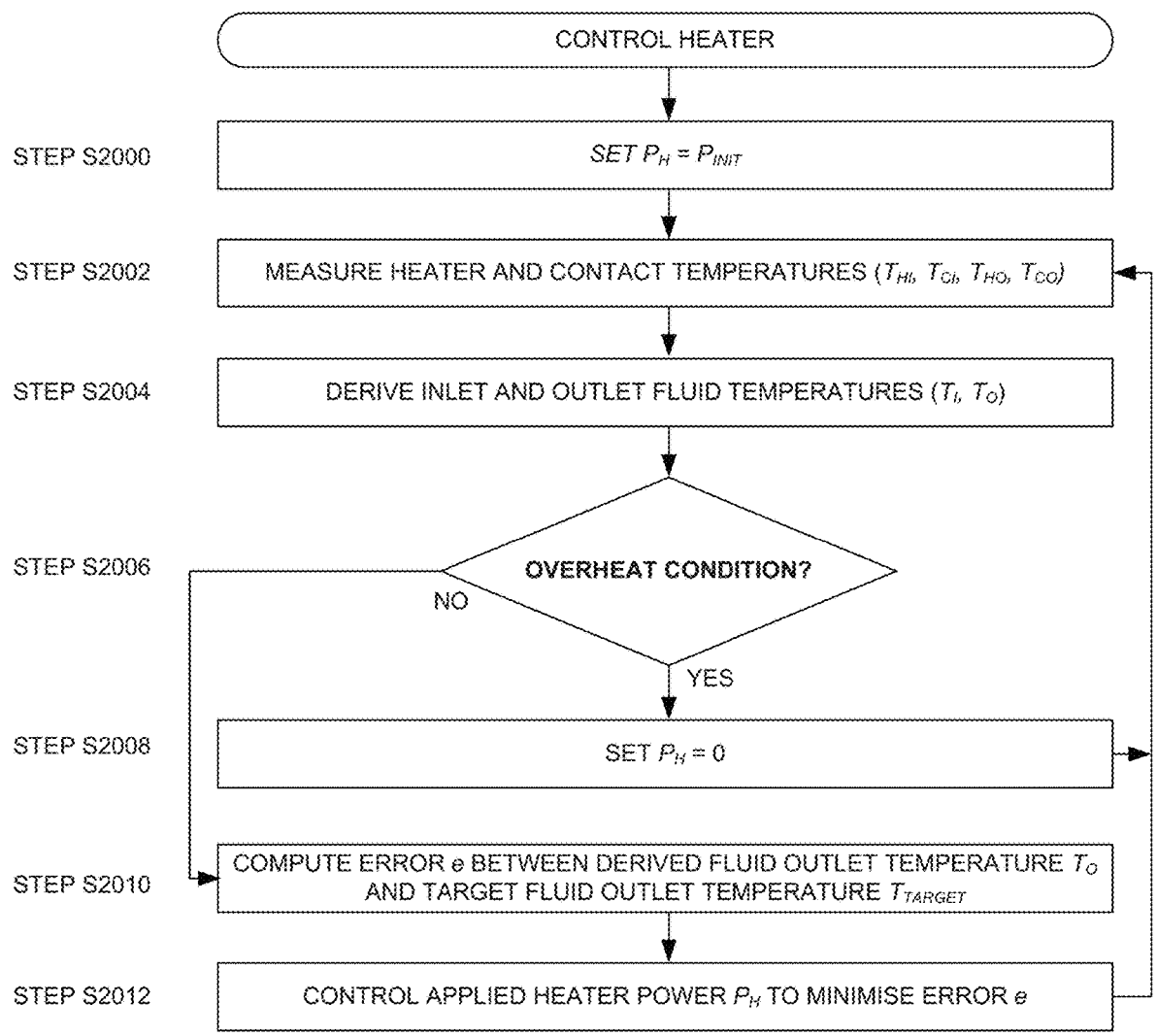
FIG. 20 is a flow chart illustrating an alternative scheme for controlling the heater of the fluid warming system of FIG. 2.

FIG. 20 is a flow chart illustrating an alternative scheme for controlling the heater of the fluid warming system of FIG. 2, which is particularly suitable with the PID controller 1400 system of FIG. 14.

Initially (step S2000) the current heater power $P_H$ is set to an initial value $P_{INIT}$, which may for example be 10 watts (W) as before. The various temperatures are measured (step S2002), heat fluxes derived (step S2004) and fluid temperatures derived (step S2006), but a fluid flow rate q is not required to be derived, though it may be for other purposes. A test is carried out (step S2008) to check whether the heater unit is overheating. If the unit is overheating, the heater power $P_H$ is reset to zero (step S2010) and the loop restarts (step S2002). If, on the other hand, there is no overheat condition, in step S2012 an error e is computed representing the difference between the derived (estimated) fluid outlet temperature $T_O$ and a target (setpoint) fluid outlet temperature $T_{TARGET}$. In step S2014 the applied heater power $P_H$ is then controlled (for example using the PID controller) to minimise the temperature error e. The control loop is then restarted at step S2002. Other control schemes and variations of the schemes described above are of course possible.

Figure 21:
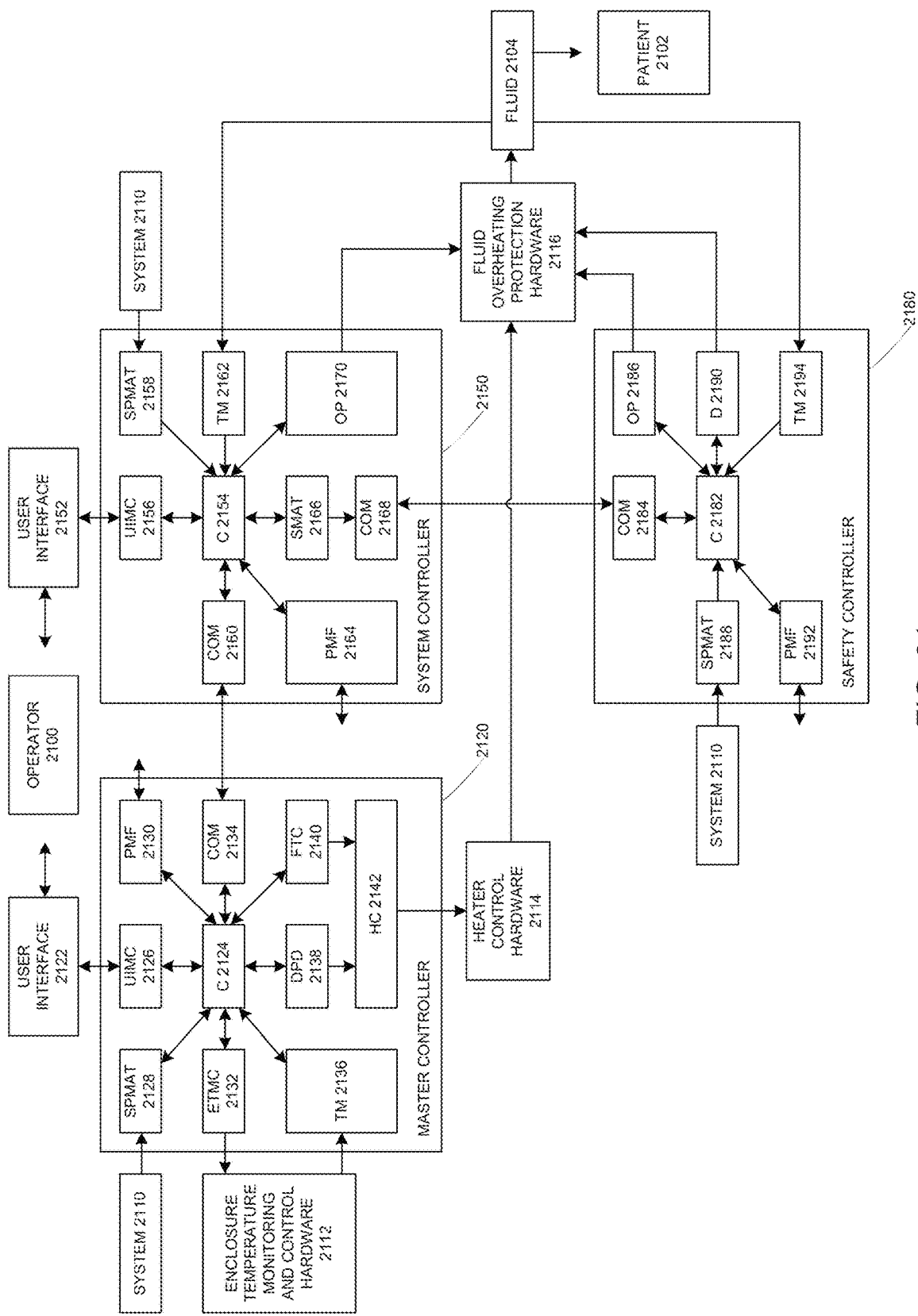
FIG. 21 is a schematic of the software and hardware architecture of the fluid warming system of FIG. 2.

FIG. 21 is a schematic of the software and hardware architecture of the fluid warming system of FIG. 2.

In overview, an operator 2100, patient 2102, fluid 2104 delivered to the patient, master controller 2120, system controller 2150 and safety controller 2180 are shown, as well as system 2110, enclosure temperature monitoring and control 2112, heater control 2114, and fluid overheating protection 2116 hardware units. For segregation and risk control, prevention of overheating the fluid is implemented as a software item separately from the temperature control functionality.

The master controller 2120 presents a user interface 2122 to the operator 2100, and comprises a core 2124, user interface monitoring and control 2126, system parameter monitoring and alarm triggering 2128, production and maintenance features 2130, enclosure temperature monitoring and control 2132, communication 2134, temperature measurement 2136, disposable presence detection 2138, fluid temperature control 2150 and heater control 2142 software units.

The core 2124 controls the main system behaviour and connected units, handles storage from and communication to connected units, and protects core functionality. The fluid temperature control 2150 monitors for internal commands and system status, enabling and disabling fluid temperature control, evaluates internal temperatures values and internal system parameters necessary for fluid temperature control, evaluates internal alarm status and sets internal heater control parameters. The production and maintenance features 2130 handles software updates, software and hardware revision communication, and reading and writing of calibration data and system specific data to and from system memory.

The system controller 2150 presents a user interface 2152 to the operator 2100 (the same as or different to interface 2122), and comprises a core 2154, user interface monitoring and control 2156, system parameter monitoring and alarm triggering 2158, first communication 2160 (for communication with the master controller), temperature measurement 2162, production and maintenance features 2164, system monitoring and alarm triggering 2166, second communication 2168 (for communication with the safety controller) and overheating prevention 2170 software units. Similar units function in similar ways with respect to the master controller 2120 above.

The safety controller 2180 comprises a core 2182, communication 2184, overheating prevention 2186, system parameter monitoring and alarm triggering 2188, diagnostics 2190, production and maintenance features 2192 and temperature measurement 2194 software units.

The control hardware and software is implemented outside the immediate patient environment, within the docking cradle shown in FIG. 9. Segregation is applied to the different controllers 2120, 2150, 2180 by having them run on different processors, each with a dedicated power supply. Furthermore the safety controller 2180 is segregated from the system controller 2150 by way of having a separate power supply, with separate system monitoring circuits. The safety controller 2180 furthermore does not share temperature calibration information with the system controller 2150, uses a dedicated temperature sensor for evaluation of the fluid temperature, does not listen to messages from the master controller (disabling its communication functionality after 2 seconds from power-up), and uses dedicated electronics for control of the protection hardware.

The embodiment shown in FIGS. 22 to 25 differs from the first embodiment shown in particular in FIGS. 6 to 9, in mostly cosmetic and ergonomic ways (for example in relation to the shape of the case). The shape of the present embodiment was preferred as giving a better trade-off between performance and usability, and complexity and cost (for example).

Figure 22:
FIG. 22 is a perspective section through the heater unit and heat exchanger unit of FIG. 3.

FIG. 22 is a perspective section through the heater unit and heat exchanger unit of FIG. 3 as assembled.

Figure 23:
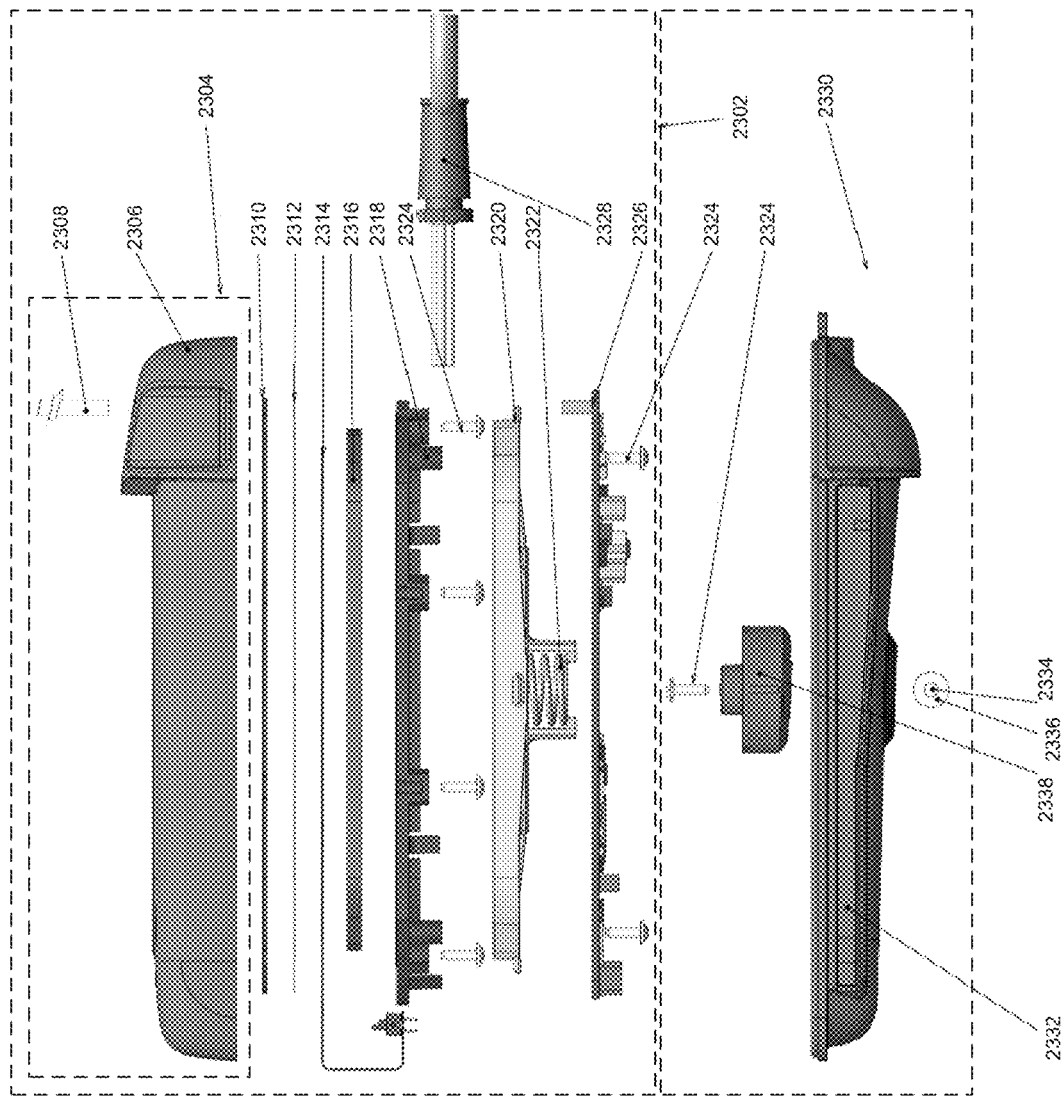
FIG. 23 is an exploded schematic of the heater unit of FIG. 3.
Figure 23:
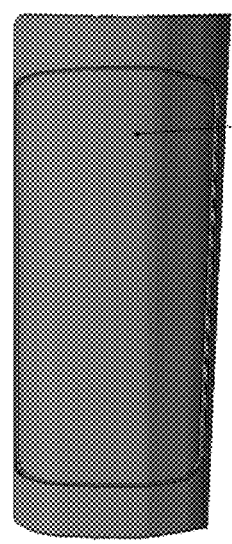

FIG. 23 is an exploded schematic of the heater unit of FIG. 3. In FIG. 23 is shown a top assembly 2302, a top cover and lightguide assembly 2304, the upper cover 2306, the light guide 2308, a foil seal 2310, an 0.075 mm thickness sheet of Kapton® (or similar polyimide) 2312, a heater assembly 2314, a foam layer 2316, an inner frame 2318, a chassis 2320, a spring activator 2322, Ejot® screws WN5451 25×8 (or similar screw or other fastener) 2324, a PCB assembly 2326, a cable assembly 2328, a bottom assembly 2330, an overmoulded lower cover 2332, a plunger shaft 2334, a guiding wheel 2336, an activator 2338, and a slider 2340.

Figure 24:
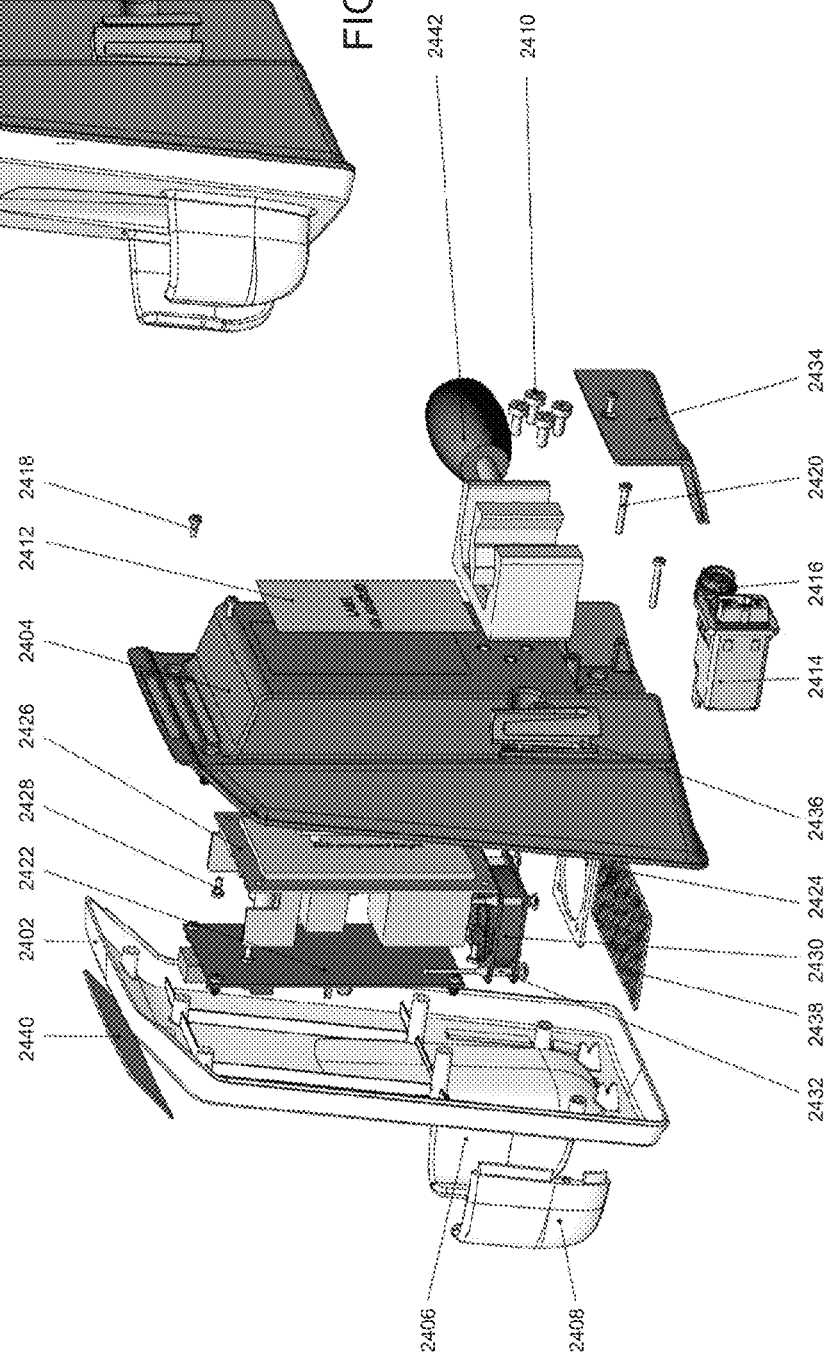
FIG. 24 is an exploded schematic of the docking cradle of FIG. 9.

FIG. 24 is an exploded schematic of the docking cradle of FIG. 9. In FIG. 24 is shown a front cover 2402, a back cover 2404, a left cradle 2406, a right cradle 2408, a screw of type M5×12 (or similar screw or other fastener) 2410, a label 2412, a network connector 2416, a data port 2416, a screw of type M3×8 (or similar fastener, and so on) 2418, a screw of type M3×25 (or similar fastener) 2420, board 2422, a frame plate 2424, a power supply 2426, a screw of type M3×8 (or similar fastener) 2428, a fan 2430, a damper 2432, a connector plate 2434, a drip chamber holder 2436, a baffle plate 2438, a front label 2440 and a clamp 2442.

Figure 25:
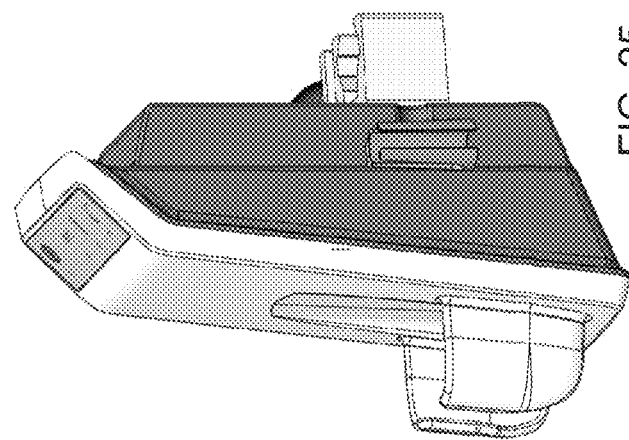
FIG. 25 is a schematic of the docking cradle of FIG. 9 as assembled.

FIG. 25 is a schematic of the docking cradle of FIG. 9 when assembled.

Figure 26A:
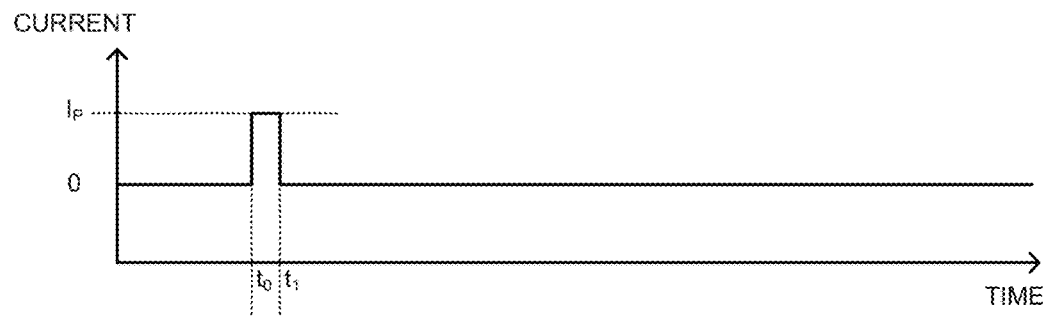
FIGS. 26A and 26B are graphs illustrating a control scheme for detecting the presence of the heat exchange unit of FIG. 3.
Figure 26B:
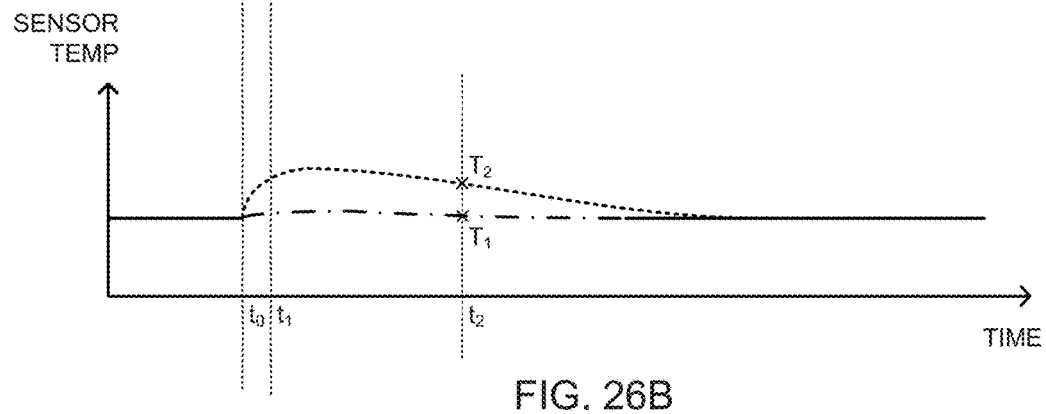

FIGS. 26A and 26B are graphs illustrating a control scheme for detecting the presence of the heat exchange unit of FIG. 3.

This scheme is a detection routine which can be called by other parts of the system, for example to ensure that a heat exchange unit (also referred to as 'cartridge' or 'disposable') is present before turning on the heater, and so on. The detection is executed by applying a short power pulse of typically 150 ms to the heating element (after heat exchange unit lock detection) and measuring the response of all heater temperature sensors. The temperature rise of the sensors is evaluated against predetermined thresholds. With no disposable in place the temperature rise will be significantly bigger than the rise measured with the disposable in place. Using this method enables the system to detect heat exchange unit placement, as well as good heater contact and placement of other objects than the intended unit.

The detection starts when all heater temperatures are below 45 degrees C. and the heater unit has been closed (in the normal course of events, so as to retain the heat exchanger in place). A 'detection busy' flag is set to prevent other processes intervening, and current heater temperatures are saved. Next, (at time $t_0$) the heater is fired with full power for a short period of time; the heater power is kept at full scale while the pulse duration is not exceeded, as shown by the current pulse (showing the current supplied to the heater elements) in FIG. 26A. When the pulse time (at time $t_1$) has ended, the heater output is disabled.

The temperature as measured by sensors in the heater unit, the output of one of which is shown in FIG. 26B, is then evaluated for a further period of time (up until time $t_2$). During the evaluation time, the highest temperature for every heater sensor is saved. The highest temperatures are recorded until the end of the evaluation time (at time $t_2$). The heater temperatures are evaluated against lower and upper limits. If the highest heater temperature difference is below the lower threshold, it is concluded that no heat exchange unit is installed (there is probably no connection with the heater at all). If the highest heater temperature difference is above the higher threshold, again it is concluded that no heat exchange unit has been installed either. In FIG. 26B, the dotted line corresponds to a typical response when a heat exchange unit is not installed, and the dotted and dashed line corresponds to a typical response when a heat exchange unit is installed and in good thermal contact with the heater unit.

A 'disposable placed' flag is set if a heat exchange unit was detected, and the 'detection busy' flag is cleared.

The use of a second outlet contact temperature sensor has been mentioned above, but any number of further outlet or inlet temperature sensors may be provided in order to improve the redundancy and reliability of the control system. For example if 3 outlet contact temperature sensors are provided, the results could be combined in a voting system whereby a clearly erroneous reading could be identified if the two other results agreed to a sufficiently close margin (and could also permit continued operation of the system if need be, for example in an emergency situation, by choosing whichever results was agreed on by at least two sensors). A similar process could be used for the inlet sensors, and additional sensors such as the intermediate sensors 818, 824 of FIG. 8 could be included, for example to improve the accuracy of the previously presented calculations, or to provide additional verification or redundancy.

The response of heater temperature sensors may vary from heater unit to heater unit, so there may be an additional step of individually calibrating each heater unit and/or temperature sensor, for example by carrying out benchmark measurements with the heat transfer unit in place and absent. As a result, the predetermined thresholds mentioned above may be determined. The thresholds may also be varied, as appropriate, depending on the type or particular model number (and so on) of the heat transfer unit (cassette) which is expected to be attached. Additionally, properties of the attached heat transfer unit (such as the type) may be inferred from the results of the process described above.

Figure 27:
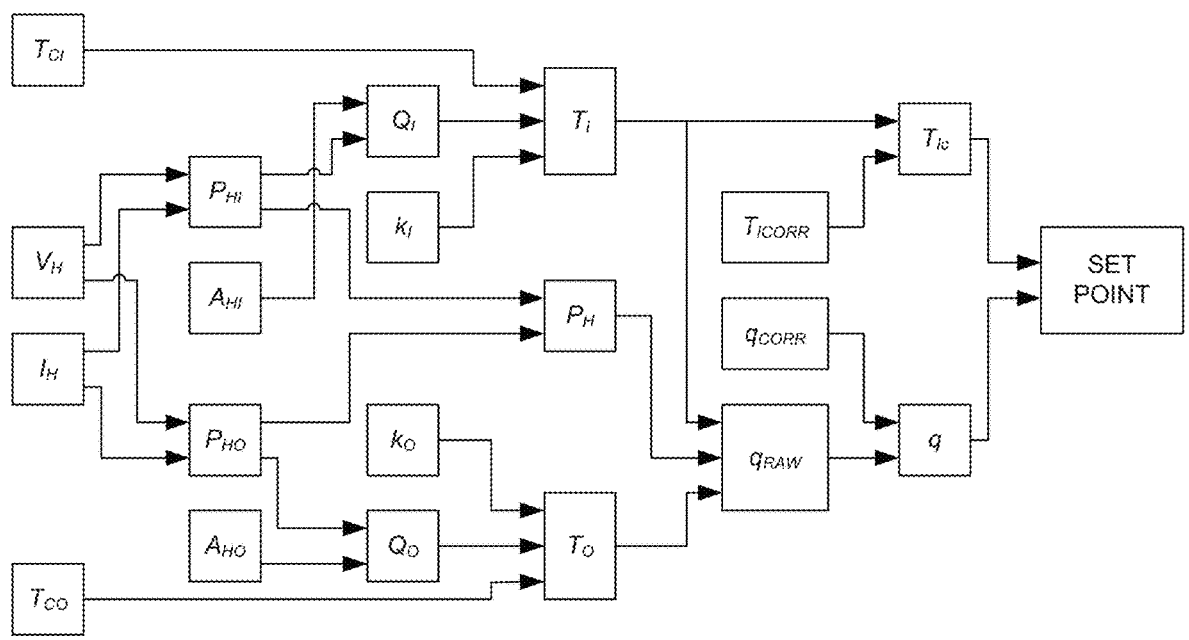
FIG. 27 is a diagram illustrating the data flow and dependencies of the alternative control scheme of FIG. 19.

FIG. 27 is a diagram illustrating the data flow and dependencies of the first version of the alternative control schemes discussed above with reference to FIG. 19. As is explained above in relation to FIG. 19, $T_{CI}$ and $T_{CO}$ are the inlet and outlet contact temperature measurements, as before. $V_H$ and $I_H$ are the voltage and current supplied to the heater elements, from which the inlet and outlet heater power $P_{HI}$, $P_{HO}$ can be derived, as a relevant proportion (⅗ and ⅖ respectively) of the overall power $P_H$, $A_{HI}$ and $A_{HO}$ are the heater areas of each element (in this case the same area $A_H$ for both inlet and outlet heater element, as they are identical in size and shape, but this is not necessarily the case). The heat fluxes $Q_I$, $Q_O$ at the inlet and outlet are derived from the relevant power $P_{HI}$, $P_{HO}$ and hearer area $A_{HI}$, $A_{HO}$. From these, inlet and outlet fluid temperatures $T_I$, $T_O$ are derived. The total heater power $P_H$ and derived inlet and outlet fluid temperatures $T_I$, $T_O$ are then processed as explained above to derive an uncorrected/raw fluid flow rate estimate $q_{RAW}$. An appropriate correction $q_{CORR}$ is applied to generate a refined estimate of fluid flow rate q. Similarly, a correction $T_{ICORR}$ is applied to the inlet temperature estimate $T_I$ to generate a refined estimate $T_{Ic}$ of fluid inlet temperature. The refined estimates of inlet temperature $T_{Ic}$ and fluid flow rate q are then used (for example in conjunction with a required heating power function as illustrated in FIG. 11) to determine an appropriate power setpoint.

Other data dependencies and formulae to derive flow rates and other quantities are of course possible.

Figure 28A:
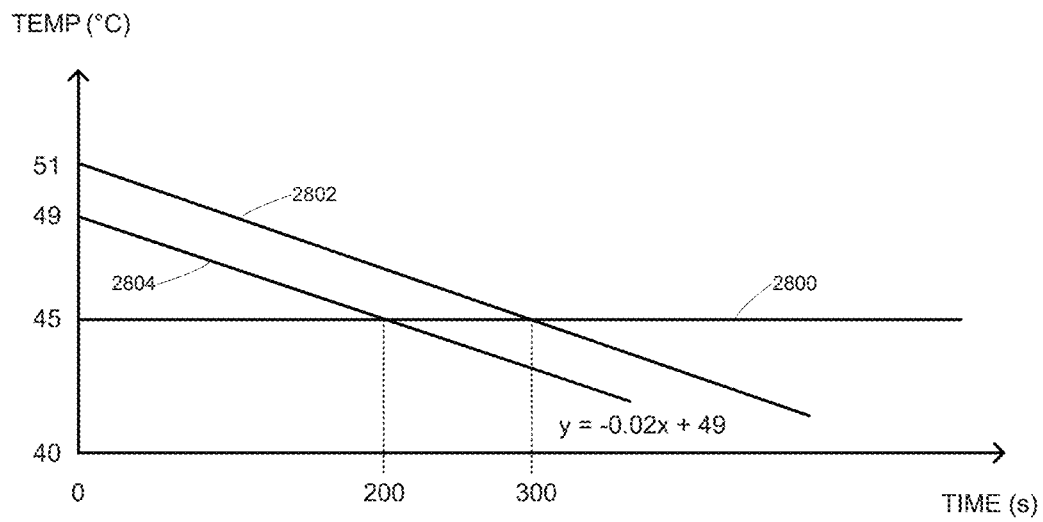
FIGS. 28A and 28B are graphs illustrating a feature of the overheating protection system of FIG. 15.
Figure 28B:
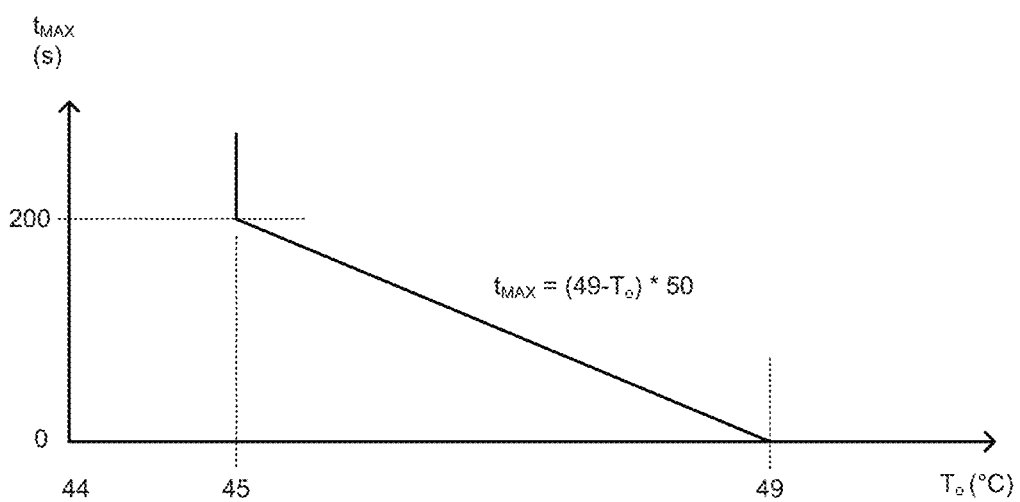

FIGS. 28A and 28B are graphs illustrating a feature of the overheating protection system mentioned above.

FIG. 28A is a graph showing the limit line for the fluid outlet temperature (approximated by $T_o$ mentioned above), for example conforming to standards such as the American standard for blood warmers. The overheating mechanism is designed to activate when the calculated temperature ($T_o$) is above a defined limit for a period of time as defined in FIG. 28A. Line 2800 represents the temperature of 45 degrees centigrade. Line 2802 represents the American blood warmer standard limit, for a time between 0 and 5 minutes. Line 2804 represents a safety margin of 2 degrees centigrade below the limit illustrated by line 2802. The line 2804 is used by the safety controller so as to ensure an appropriate safety margin of operation. The equation for the safety limit line is also indicated in the figure.

FIG. 28B is a graph showing the maximum heating time permitted for a particular derived outlet temperature $T_o$, based on the limit shown in FIG. 28A. The equation for the safety limit line is indicated in the figure.

The other safety restrictions mentioned above in relation to Figure @ also apply.

Although the embodiments above predominantly relate to warming IV fluids, it will be appreciated that the same principles can apply for example to preventing icing of water in external pipes, or to warming bodily fluids for other purposes (for example to treat hypothermia), and so on.

Although the present invention has been described above with reference to specific embodiments, it will be apparent to a skilled person in the art that modifications lie within the spirit and scope of the present invention.

The invention claimed is:

1. A fluid warming system for warming fluid for intravenous use, comprising:
   a heater unit, including a heating element and at least one temperature sensor;
   a heat exchanger unit, removably attachable to the heater unit, which includes an inlet and an outlet through which a fluid for intravenous use can pass, and
   a controller, programmed:
      to receive at least one temperature measurement from said at least one temperature sensor in the heater unit;
      to process said at least one temperature measurement to determine a temperature difference between the inlet and outlet;
      to compute a fluid flow rate, corresponding to the rate of flow of fluid from the inlet to the outlet of the heat exchanger unit, in proportion to an amount of electrical power supplied to the heating element divided by said temperature difference; and to control the electrical power supplied to the heating element in dependence on the computed fluid flow rate to cause the fluid to be warmed.

2. A fluid warming system according to claim 1, wherein the controller is further programmed:
to compute an inlet fluid temperature in dependence on a first of said at least one temperature measurement, measured in thermal proximity to the inlet, and the electrical power supplied to the heater element;
to compute an outlet fluid temperature in dependence on a second of said at least one temperature measurement, measured in thermal proximity to the outlet (308), and the electrical power supplied to the heater element; and
to carry out the step of computing a fluid flow rate in dependence on the computed inlet and outlet fluid temperature.

3. A fluid warming system according to claim 2, wherein the controller is further programmed:
to compute said inlet fluid temperature as the difference between a value dependent on the first of said at least one temperature measurement and a first value proportional to the electrical power supplied to the heater element; and
to compute said outlet fluid temperature as the difference between a value dependent on the second of said at least one temperature measurement and a second value proportional to the electrical power supplied to the heater element.

4. A fluid warming system according to claim 3, wherein the controller is further programmed:
to compute said value dependent on the first of said at least one temperature measurement as a value proportional to the first said at least one temperature measurement added to an inlet temperature correction value; and
to compute said value dependent on the second of said at least one temperature measurement as a value proportional to the second said at least one temperature measurement added to an outlet temperature correction value.

5. A fluid warming system according to claim 1, wherein said at least one temperature sensor in the heater unit comprises:
at least one inlet temperature sensor in thermal proximity to the inlet of the heat exchanger unit, when attached; and
at least one outlet temperature sensor in thermal proximity to the outlet of the heat exchanger unit, when attached.

6. A fluid warming system according to claim 5, wherein none of said at least one temperature sensors are in physical contact with the fluid.

7. A fluid warming system according to claim 1, wherein the controller is programmed, in at least one operating mode, to control the electrical power supplied to the heating element so as to cause the electrical power to converge on a target heater power selected in dependence on the computed fluid flow rate.

8. A fluid warming system according to claim 7, wherein the target heater power is selected in accordance with an expected relation between the heater power and a target outlet fluid temperature at the computed fluid flow rate.

9. A fluid warming system according to claim 7, wherein the controller is programmed, in at least one further operating mode, to cease the supply of electrical power to the heating unit.

10. A fluid warming system according to claim 1, wherein the controller is programmed, in at least one operating mode, to control the electrical power supplied to the heating element so as to cause the computed outlet fluid temperature to converge on a target temperature.

11. A fluid warming system according to claim 10, wherein the target temperature is selected in dependence on the computed fluid flow rate.

12. A fluid warming system according to claim 1, wherein the heater unit is electrically isolated from the heat exchanger unit.

13. A fluid warming system according to claim 1, wherein the heating element includes a plurality of sub-elements, and different amounts of electrical power are supplied to different sub-elements.

14. A fluid warming system according to claim 13, wherein a greater amount of electrical power is supplied to a sub-element in the vicinity of the inlet of the heat exchanger unit than is supplied to a sub-element in the vicinity of the outlet of the heat exchanger unit.

15. A fluid warming system according to claim 1, wherein the heat exchanger unit is connectable to a fluid conduit for transferring the fluid to or from a fluid channel within the heat exchanger unit, wherein the surface area per length of the fluid channel is larger than the surface area per length of fluid conduit.

16. A fluid warming system according to claim 1, wherein the controller is further programmed:
to compute an inlet heat flux corresponding to the heat flux between the heating element and the fluid in the vicinity of the inlet of the heat exchanger unit;
to compute an outlet heat flux corresponding to the heat flux between the heating element and the fluid in the vicinity of the outlet of the heat exchanger unit;
to compute an inlet fluid temperature in dependence on the computed inlet heat flux;
to compute an outlet fluid temperature in dependence on the computed outlet heat flux; and
to carry out the step of computing a fluid flow rate in dependence on the computed inlet and outlet fluid temperature.

17. A fluid warming system according to claim 16, wherein at least one of the computed inlet and outlet heat fluxes his computed as a ratio of the electrical power supplied to the heater element in the vicinity of the inlet or outlet respectively, and an area of the heater element exposed to the heat exchanger unit in the vicinity of the inlet or outlet respectively.

18. A fluid warming system according to claim 16, wherein at least one of the computed inlet and outlet heat fluxes is computed in dependence on a temperature difference between the heating element and the heat exchanger unit in the vicinity of the inlet and outlet respectively.

19. A fluid warming system according to claim 1, wherein the controller is programmed to control the electrical power supplied to the heating element using a PID controller.

20. A method of operating a fluid warming system to warm fluid for intravenous use, the fluid warming system comprising a heater unit, including a heating element and at least one temperature sensor, and a heat exchanger unit, removably attachable to the heater unit and including an inlet and an outlet through which a fluid for intravenous use can pass, and the method comprising:

receiving at least one temperature measurement from said at least one temperature sensor in the heater unit;

processing said at least one temperature measurement to determine a temperature difference between the inlet and outlet;

computing a fluid flow rate, corresponding to the rate of flow of fluid from the inlet to the outlet of the heat exchanger unit, in proportion to an amount of electrical power supplied to the heating element divided by said temperature difference; and controlling the electrical power supplied to the heating element in dependence on the computed fluid flow rate to cause the fluid to be warmed.

21. A method according to claim 20, wherein controlling the electrical power supplied to the heating element comprises controlling the electrical power using a PID controller.

22. A computer readable medium tangibly embodying computer program code for use with a fluid warming system to warm fluid for intravenous use, said fluid warming system comprising a heater unit, including a heating element and at least one temperature sensor, a heat exchanger unit, removably attachable to the heater unit and including an inlet and an outlet through which a fluid for intravenous use can pass, and at least one processor and associated memory, the computer program code being operable, when stored in said memory and executed by said at least one processor, to cause said fluid warming system to:

receive at least one temperature measurement from said at least one temperature sensor in the heater unit;

process said at least one temperature measurement to determine a temperature difference between the inlet and outlet;

compute a fluid flow rate, corresponding to the rate of flow of fluid from the inlet to the outlet of the heat exchanger unit, in proportion to an amount of electrical power supplied to the heating element divided by said temperature difference; and control the electrical power supplied to the heating element in dependence on the computed fluid flow rate to cause the fluid to be warmed.

23. A computer readable medium according to claim 22, wherein the computer program code is further operable to control the electrical power supplied to the heating element using a PID controller.

* * * * *